United States Patent [19]

Miller

[11] Patent Number: 5,532,139
[45] Date of Patent: * Jul. 2, 1996

[54] MICRO LYSIS-ANALYSIS PROCESS TO MEASURE CELL CHARACTERISTICS AND DIAGNOSE DISEASES

[75] Inventor: Frederick N. Miller, Louisville, Ky.

[73] Assignee: Micro-Med, Inc., Louisville, Ky.

[ * ] Notice: The portion of the term of this patent subsequent to Oct. 30, 2012, has been disclaimed.

[21] Appl. No.: 414,376

[22] Filed: Mar. 31, 1995

Related U.S. Application Data

[63] Continuation-in-part of Ser. No. 969,764, Oct. 30, 1992.
[51] Int. Cl.⁶ .................................................. C12Q 1/02
[52] U.S. Cl. .............................. 435/29; 435/7.2; 436/10; 436/63; 436/172; 436/902; 422/55; 422/73; 422/82.05; 324/71.4; 324/71.1
[58] Field of Search ................................ 435/29, 34, 7.2, 435/70.4; 436/10, 17, 63, 164, 172, 519, 902; 422/55, 73, 82.5, 82.7; 324/71.1, 71.4

[56] References Cited

U.S. PATENT DOCUMENTS

| | | | |
|---|---|---|---|
| 3,882,385 | 5/1975 | Coulter et al. | 324/71.1 |
| 4,220,916 | 9/1980 | Zimmermann et al. | 324/71.1 |
| 4,278,936 | 7/1981 | Shine | 324/71.1 |
| 4,374,644 | 2/1983 | Armstrong | 436/63 |
| 4,491,012 | 1/1985 | Peterson | 73/61.63 |
| 4,535,284 | 8/1985 | Groves et al. | 324/71.1 |
| 4,599,307 | 7/1986 | Saunders et al. | 435/34 |
| 4,656,139 | 4/1987 | Matsuda et al. | 436/17 |
| 4,657,851 | 4/1987 | Feller et al. | 435/7.23 |
| 4,797,606 | 1/1989 | Fahn et al. | 324/71.1 |
| 4,835,457 | 5/1989 | Hauds et al. | 324/71.4 |
| 4,882,284 | 11/1989 | Kirchanski et al. | 436/63 |
| 5,057,413 | 10/1991 | Terstappen et al. | 435/6 |
| 5,128,245 | 7/1992 | Greenberg et al. | 435/29 |

FOREIGN PATENT DOCUMENTS

0209526  5/1984  Germany.

OTHER PUBLICATIONS

Acquaye et al., The Development of a Filtration System For Evaluating Flow Characteristics of Erythrocytes; Microvasc. Res. 33:1–14, 1987.

Araki et al., The Rate of Osmotic Hemolysis, A Relationship with Membrane Bilayer Fluidity, Biochimica et Biophysica Aeta 645:81–90, 1981.

Actmann G., A Microscopic Photometric Method For Measuring Erythrocyte Deformability, Clinical Hemorheology 6:617–627, 1986.

Blum, H. F., Photodynamic Hemolysis—Modes of Inhibition, Journal of Cellular and Comparative Physiology 9:229–239, 1937.

Blum, et. al., Photodynamic Hemolysis III, The Percentage of Hemolysis Curve, Journal of Cellular and Comparative Physiology 13:269–279, 1939.

Clark, et al., Osmotic Gradient Ektcytometry: Comprehensive Characterization of Red Blood Cell Volume and Surface Maintenance, Blood 61:899–910, 1983.

Cummings et al., Effects of Pentoxifylline and Metabolite on Red Blood Cell Deformability as Measured by Ektacytometry, Angiology 41:118–123, 1990.

De Geoij et al., Photodynamic Effects of Protoporphyrin on Cholesterol and Unsaturated Fatty Acids in Erythrocyte Membranes in Protoporphyria and In Normal Red Blood Cells, Clin. Chin. Acta. 68–115–122, 1976.

(List continued on next page.)

Primary Examiner—Jill Warden
Assistant Examiner—Harold Y. Pyon
Attorney, Agent, or Firm—Middleton & Reutlinger; David W. Carrithers

[57]   ABSTRACT

A microphotolysis and microphotoanalysis process applying precise quantities of focused light energy to a precise microscopic area of a very small cell sample to activate a chemical agent which permits measurement of cell fragility.

44 Claims, 22 Drawing Sheets

OTHER PUBLICATIONS

Deuticke et al., Formation of Aqueous Pores in the Human Erythrocyte Membrane After Oxidative Cross–Linking of Spectrin by Diamide, Biochim. et. Biophys. Acta. 731:196–210, 1983.

Deuticke et. al., Ion Selectivity of Aqueous Leaks in the Erythrocyte Membrane by Cross–Linking of Membrane Proteins, Biochimica et Biophysica Acta, 775:150–160, 1984.

Dougherty, T. J., Photosensitizers: Therapy and Detection of Malignant Tumors, Photochem. Photobiol. 45:879–889, 1987.

Fabry et al., An Objective Sign in Painful Crisis in Sickle Cell Anemia, The Concomitant Reduction of High Density Red Cells, Blood 64:559–563, 1984.

Feo et al., Role of ATP Depletion on Red Cell Shape and Deformability Red Cell Rheolagy, ed. M. Bessis, Shobet, and Mohandas, Springer–Verlag Berlin, Heidelberg, N.Y. 1978, pp. 153–157.

Ferrell et al., Phosphoinositide Metabolism and The Morphology of Human Erythrocytes, J. Cell Biol. 98:1092–1998, 1984.

Fischer et al., Selective Alteration of Erythrocyte Deformability by SH–reagents; Evidence For an Involvement of Spectrin in Membrane Shear Elasticity, Biochim. et Biophys. Acta. 510:270–282, 1978.

Fleischer et al., Mechanism of in vivo Photohemolysis in Erythropoietic Protoporphyria, J. Invest. Dermatol. 46:505–509, 1966.

Girotti, A. W. Photodynamic Lipid Peroxidation in Biological Systems, Photochemistry and Photobiology 51:497–509, 1990.

Hebbel, R. P. The Sickle Erythrocyte in Double Jeopardy: Autoxidation and Iron Decompartmentalization, Seminars in Haematology 25:51–69, 1990.

Kuwabara et al., Mechanisms of Photosensitization by Pheophorbide as Studied by Photohemolysis of Erythrocytes and Electron Spin Resonance Spectroscopy, Photochem. and Photobiol. 49:37–41, 1989.

Lipowsksy et al., Human SS Red Cell Rheological Behavior in Microcirculation of the Cremaster Muscle, Blood Cells 8:113–126, 1982.

Mayhan et al., The Effects of Altering the External Calcium Concentration and a Calcium Channel Blocker, Verapamil on Microvascular Leaky Sites and Dextran Clearance in the Hamster Check Pouch, Microvasc. Res. 28:159–179, 1984.

Messman et al., Mechanical Properties of Sickle Cell Membranes, Blood 75:1711–1717, 1990.

Minetti et al., Involvement of Erythrocyte Skeletal Proteins in the Modulation of Membrane Fluidity by Phemothiazimos, Biochemistry 26:8133–8137, 1987.

Mohandas et al., The Influence of Membrane Skeleton on Red Cell Deformability Membrane Material Properties and Shape, Seminars in Hemotology 20:225–242, 1983.

Mohandas et al., Analysis of Factors Regulating Erythrocyte Deformability, J. Clin. Invest., 66:563–573, 1980.

Pooler et al., Photohemolysis of Human Erythrocytes Labeled in Band 3 with Eosin–Isothiocynate, Photochemistry and Photobiology 44:495–499, 1986.

Poser et al., Formation of Aqueous Pores in the Human Erythrocyte Membrane After Oxidative Crosslinking of Spectrim by Diamide, Biochimica et Biophysica Acta 731:196–210, 1983.

Quist et al., Polyphosphoinositides and the Shape of Mammalian Erythrocytes, Lipids 20:433–438, 1985.

Reinhart et al., The Time Course of Filtration Test as a Model For Microvascular Plugging by White Cells and Hardened Red Cells, Microvasc. Res. 34:1–12, 1987.

Rosso et al., Influence of Chlorpromazine on the Transverse Mobility of Phospholipids in the Human Erythrocyte Membrane: Relation to Shape Changes, Biochimica et Biophysica Acta. 942:271–279, 1988.

Schothorst et al., Metabolic Aspects of the Photodynamic Effect of Protoporphyrin in Protoporphyria and in Normal Red Blood Cells, Clin. Chim. Acta. 33:207–213, 1971.

Shohet et al., Possible Roles for Membrane Protein Phosphorlyation in the Control of Erythrocyte Shape, in "*Red Cell Rheology*" (ed. Bessis, Shohet, and Mohandes, Springer–Verlag, Berlin, Heidelberg and N.Y. 1978, pp. 115–131.

Sowemimo–Coker et al., The Effect of Pentoxifylline on Filterability of Normal Red Blood Cells and Their Adhesiveness to Cultured Endothelial Cells, Eur. J. Clin., Pharmacol. 29:55–59, 1985.

Svensjo et al., The Effects of Intermittent and Continuous Stimulation of Microvessels in the Check Pouch of Hamsters with Histamine and Brady Kinin on the Development of Venular Leaky Sites, Microcirc. Endothel. and Lymphat, 1:381–396, 1984.

Valenzeno et al., Measurement of Cell Lysis by Light Scattering, Photochem. and Photobiol. 42:335–339, 1985.

Valenzeno, D. P., Photomodification of Biological Membranes with Emphasis on Singlet Oxygen Mechanisms, Photochemistry and Photobiology 46:147–160, 1987.

Verweij et al., Photodynamic Protein Cross–Linking, Biochmiica et Biophysica Acta 646:87–94, 1981.

Weishaupt et al., Identification of Singlet Oxygen as the Cytotoxic Agent in Inactivation of a Murine Tumor, Cancer Res, 36:2326–2329, 1976.

Miller et al. Quantitation of Erythrocyte Photohemlysis by Light Microscopy.

Miller et al., Use of Microphotohemolysis to Distinguish Differences in Erythrocyte Treatments.

MICRO LYSIS-ANALYSIS PROCESS TO MEASURE CELL CHARACTERISTICS AND DIAGNOSE DISEASES

This application is a Continuation-In-Part of U.S. patent application Ser. No. 07/969,764 filed on Oct. 30, 1992.

BACKGROUND OF THE INVENTION

Under various cell environments, most biological cells can drastically change their shape (called cell "deformability") without structural damage to the cell membrane, without a loss in cell contents to the cell environment, and without a change in the chemical function of the cell membrane. Under other cell environments, the cell membrane can lose chemical function, can suffer structural damage, and can rupture to lose cell contents to the cell environment (called cell fragility). Thus, cell deformability and cell fragility are two independent characteristics of a cell membrane. Cells can have any combination of a high-to-low deformability and a high-to-low fragility. However, most normal cells have high deformability and moderate-to-low fragility.

Deformability is one important characteristic for some cells such as "sensory receptors" which are normally stationary in the cell environment and for other cells such as blood and lymph cells which normally move in the cell environment. Cell fragility is an important characteristic for almost all normally stationary and normally moving cells because changes in the cell environment can cause considerable amounts of water to move into cells to rupture more fragile cells. Changes in cell fragility can change the ability of a cell to perform its normal function in a normal or abnormal cell environment. For example, an abnormally high fragility of red blood cells will lead to premature rupture of many red blood cells in a normal blood environment which will reduce the circulating pool of red blood cells and will reduce the red blood cell transport of oxygen to tissues. Yet, these highly fragile cells can have normal cell deformability. Thus, fragility might clinically be a more important cell characteristic than deformability.

Cell fragility is altered by many conditions such as cell age, duration of blood-bank storage, treatment with a variety of membrane-binding drugs, and progression of membrane or hemoglobin-related diseases such as diabetes and sickle-cell anemia, respectively. Thus, a rapid, highly accurate, and easily applied method is needed for clinical measurements to assess cell fragility as an index of "cell strength" which is defined as the degree to which the cell membrane can maintain its structural integrity and its chemical function in a normal and an altered cell environment. Most current methods for assessing cell strength primarily create mechanical forces on cells to assess either the deformability or the fragility of these cells. These methods include Osmotic-Gradient Ektacytometry, and Cell Filtration, Micropipette Suction, and Osmotic Fragility tests.

Osmotic-Gradient Ektacytometry is one method that applies mechanical forces to measure a combination of cell deformability and cell fragility. This method uses a viscometer device to measure shape changes which are induced in red blood cells by various speeds of rotation (called applied shear stress) of the test cells with different osmotic solutions in the cell environment. The osmotic-spectrum curves which are produced by Ektacytometry are highly variable for the same test-cell sample due to small changes in sample ambient temperature, pH, and plasma osmolality. Thus, these osmotic-spectrum curves are complex and very difficult to use for interpretation of changes in cell deformability. As a result, Ektacytometry currently requires very sophisticated equipment, extensive operator training, and highly controlled test conditions to obtain one measurement value for the combination of cell deformability and fragility. This makes Ektacytometry usable only in a few research laboratories and not in a clinical setting.

Other methods such as Cell Filtration and Micropipette Suction also require the external application of a mechanical force to cells but these methods primarily measure cell deformability by forcing (filtering) cells through various size pores or by mechanical aspiration of these cells into micropipettes of fixed tip size and taper. These methods also require very sophisticated equipment and substantial operator training; and they are extremely time consuming to obtain an analysis of only a relatively few cells in each test-cell sample. Thus, these methods have also not been accepted into general clinical use.

Assessment of cell deformability in the Cell Filtration method has been improved by measurements of electrical impedance (Hanss et al, U.S. Pat. No. 4,835,457) and measurements of time (David D. Paterson, U.S. Pat. No. 4,491,012) during the application of external mechanical force (pressure) to force red blood cells to pass through either an artificial membrane filter or a foil system (Helmut Jahn, U.S. Pat. No. 4,797,606). These measurement methods are extremely sensitive to manufacturing tolerances on the filter or foil and both of these measurement methods primarily assess only cell deformability and not cell fragility. Thus, these measurement additions to the Cell Filtration method have also not found their way into common clinical use.

The Osmotic Fragility method was one of the earliest techniques that was developed for assessment primarily of red blood cell fragility rather than deformability, and it is one of the few methods currently in clinical use. The Osmotic Fragility method is time-consuming, and it requires multiple blood handling steps, and relatively large volumes of blood samples. The Osmotic Fragility method uses exposure of blood samples to a large range of salt concentrations to produce a large range in the osmotic pressure for the cell environment. The osmotic pressure mechanically forces water into cells to swell cells to the point of cell membrane rupture.

The osmotic pressure method has been adapted by Groves and Rodriguez (U.S. Pat. No. 4,535,284) to apply high frequency and low frequency electrical currents to detect the percent of red blood cells that are altered during application of osmotic mechanical forces over a large range of osmotic cell environments. This use of high frequency and low frequency electrical currents is combined with a Coulter Counter® to classify individual red blood cells as normal or abnormal.

Overall, the osmotic mechanical gradient method and various refinements to this method can only detect relatively large changes in cell membrane fragility because this osmotic-based mechanical method provides no information about the rate of cell lysis (which occurs when the cell membrane ruptures). The lack of method sensitivity to mild or moderate changes in cell fragility has led to the clinical use of the osmotic mechanical method only for diagnosis of one disease called hereditary spherocytosis.

In contrast to methods that apply external mechanical forces mostly to measure cell deformability or in one case (osmotic gradients) to measure cell fragility, there is a chemical method which changes the mechanical characteristics of cell membranes to assess cell membrane fragility. It was first shown some fifty years ago that some chemicals can be changed by light (called photoactivation) to induce the rupture or breakup of red blood cell membranes (called hemolysis) in a test tube. Since then, this basic process (called photohemolysis) has been extensively studied in a variety of test-tube experiments.

The mechanism for photohemolysis is oxygen dependent and is thought to involve the generation of singlet oxygen with the subsequent oxidation of proteins in the red blood cell membrane. It has been suggested that this protein oxidation leads to the creation of extra water channels in the cell membrane. This would increase passive cationic exchange across the cell membrane to give a subsequent influx of water into the cell to swell the cell to the point of hemolysis. It has been suggested that photohemolysis could also involve peroxidation of the lipid layers in the cell membrane. This peroxidation appears to limit the ability of molecules to move (called membrane fluidity) in the lipid bilayer of the cell membrane, which then appears to limit the ability of the cell to undergo shape changes (cell deformability), since shape changes in normal cells appear to depend on membrane fluidity in the lipid bilayer.

Thus, there is considerable scientific evidence to show that certain chemical agents can be photoactivated to create cell-attack agents which disrupt red blood cells by altering either the protein or the lipid layer of the cell membrane. These alterations in cell membrane structure permit water inflow to increase internal cell volume until the "internal cell pressure" ruptures the cell membrane (called cell fragility) sufficiently to cause the loss of cell contents (called lysis in general or hemolysis in the case of red blood cells).

Currently, a limited number of chemical agents have been identified as potential cell-attack agents. Previous research has not yet discovered an acceptable method for use of these cell-attack agents to reproducibly create photohemolysis. Previous uses of these cell-attack agents have been limited by requirements for long photoactivation periods, long analysis times, test-cell isolation from the original blood sample, multiple blood samples and high volume (milliliter) samples, and by a test result that gives only a single measurement parameter for each sample.

The long photoactivation periods have been a major limitation. For example, photoactivation of red blood cells incubated with 0.1 mM of protoporphyrin as the cell-attack agent requires approximately twenty minutes of photoactivation exposure time to achieve only a modest 20% hemolysis in the cell sample; a 100% hemolysis requires a 25-minute or longer photoactivation exposure period with this agent. Similarly, more than twenty minutes of photoactivation exposure is needed with pheophorbide as the cell-attack agent to give approximately 90% hemolysis in the cell sample. Photoactivation periods of 3–4 hours are required with eosin-isothiocyanate as the cell-attack agent to give maximal hemolysis which only then occurs approximately 11 hours after the photoactivation period. These long photoactivation periods produce highly variable hemolysis rates and hemolysis levels which have limited these photohemolysis techniques to research use.

A few researchers have previously attempted the use of a light scattering device to detect the presence of significant photohemolysis. However, this device is very sensitive to very small changes in red blood cell concentrations, and this device requires a monolayer of red blood cells with a red cell concentration of less than 0.00025%. Such concentrations have not been practicable to achieve even by current modern micropipetting systems. In addition, the use of a cell monolayer and the light scattering measurement have also been limited by a long photoactivation and hemolysis measurement period since 100% hemolysis of a cell sample requires four hours with phloxine B as the photoactivated cell-attack agent.

Current clinical methods rely on osmotic mechanical forces over a wide osmotic range to create hemolysis, and these methods require milliliter (i.e. macro) quantities of blood volumes to determine an osmolality range (equivalent to internal water pressure) within which hemolysis occurs. These Osmotic Fragility tests are generally performed on sample volumes in test tubes or cuvettes, and parallel light is required for detection of the presence or absence of significant hemolysis. These current clinical hemolysis methods cannot separately measure changes in cell deformability and cell fragility, cannot distinguish changes in cell membrane fragility due to alterations in the protein layer of the membrane from fragility changes due to alterations in the lipid layers of the membrane, and cannot determine "a rate of hemolysis" which would provide a more sensitive hemolysis test for clinical use.

Both the current Osmotic Fragility clinical method and the Photohemolysis research method require multiple cell samples, multiple sample dilutions, sample centrifugation, and separate sample analysis in a spectrophotometer to give a single measurement of a parameter called Percent Cell Hemolysis at one point in time as an assessment of cell membrane fragility. Thus, these current clinical and research methods do not provide simultaneous energy-dose dependent and time-dependent measurements of photoactivation and hemolysis relationships from one, small volume (i.e. micro), blood sample.

SUMMARY OF THE INVENTION

The present invention includes a new "micro-lysis" process which applies precise measurable quantities of focused energy to a precise microscopic area of a very small cell sample (a cell micro-sample of less than 25 μl) to activate a chemical agent (called the energy-activated cell-attack agent) which then attacks the cell membranes only in the microscopic area of the cell micro-sample. The present invention also includes a new "micro-analysis" process which measures, as a function of time, the precise degree of cell membrane rupture which is caused by the energy-activated cell-attack agent in the microscopic area of cell-attack. The combination of these two processes give a quantitative, time-related, energy-dose dependent, multi-value measure of the cell membrane property that is commonly called cell fragility.

The present invention (called the Micro Lysis-Analysis Process) has several advantages over other current methods which give relatively imprecise single-value estimates of cell fragility. The Micro Lysis-Analysis process is unique in its use of microscopic focused energy to activate the cell-attack agent only in a very small defined microscopic area of a cell micro-sample. Thus, independent cell-attack in multiple separated microscopic areas can be initiated to obtain multiple cell fragility measurements in a single micro-sample, with other microscopic areas left as baseline unactivated cell-attack sample references. Each microscopic area of a micro-sample can also be analyzed before energy activation of the cell-attack agent in each respective microscopic area to give a local microscopic baseline reference for subsequent determination of the lysis response in each respective microscopic area. In contrast to other current methods, these advantages of the present invention provide multiple "energy-dose lysis-response" relationships to give very precise time-related measurements of cell membrane fragility in a single micro-sample.

Unlike other current methods, the novel use in the present invention of focused energy on a small microscopic area of a cell micro-sample only requires relatively short energy-exposure times of 1 to 10 minutes to activate the cell-attack agent, and a relatively short time, depending on the cell population, of 30 to 60 minutes to obtain complete cell lysis. Thus, the present invention provides a unique and complete micro-lysis response curve to measure the rate as well as the final degree of cell lysis within a total measurement time of one hour or less on a single micro-sample of 25 microliters (μl) in volume.

In the present invention, precise quantities (doses) of various test chemicals can be added to the cell micro-sample to provide a dose-response test for the effect (efficacy) of those chemicals to alter cell fragility. Thus, the present invention can provide a unique and complete dose-response analysis for six doses of a test chemical on a total blood sample of 150 μl in volume.

Unlike other current methods, the present invention is a new process which does not require cell isolation from the original blood sample, multiple blood samples, or further cell manipulation after the micro-sample is placed in the sample-carrier. The present invention is easy to perform with easy-to-conduct tests of reproducibility by separate energy-activation in multiple microscopic areas of each micro-sample. The present invention is a new process which gives a micro-lysis that depends only on the level of energy-activation and on the concentration and formulation of the cell-attack agent. The present invention is a new process that is not affected (as are other methods) by variations in sample temperature which can increase Brownian cell motion to confound other lysis measurements, and is not affected by non-specific effects of other blood constituents such as plasma in the cell micro-sample. Thus, the present invention is a new process which creates a very specific energy-level related cell lysis only in the area of focused energy-activation of the cell-attack agent.

The present invention is a new process that can measure alterations in cell membrane fragility due to changes in membrane characteristics that are created by a cell-attack agent that remains and becomes activated only outside the cell (an extracellular cell-attack agent). The present invention is a new process that can also measure alterations in cell membrane fragility due to changes in internal cell structures that are created by a cell-attack agent that crosses the cell membrane to attach to internal cell structures where the cell-attack agent becomes energy-activated. Thus, the present invention is a new process which can provide first-ever detection of systemic diseases that alter only the cell membrane, systemic diseases which alter only the internal cell composition, and detection of alterations in cell fragility due to treatments of cells with test chemicals.

The energy level for activation of an intracellular cell-attack agent will in part depend on the anti-oxidant status of the cell. Many cells such as red blood cells usually carry oxygen and these cells maintain a well developed anti-oxidant system to protect the cell against auto-oxidation. Other current methods to assess cell fragility cannot also assess anti-oxidant activity because these other methods do not induce oxidation reactions within the cell. The present invention is a new process which can measure the difference in cell fragility due to energy-activation of separate external and internal cell-attack agents to determine the status of the anti-oxidant system in the cell.

The present invention is a new process (called a Micro Lysis-Analysis Process) which uses a generally known configuration of generally available equipment, new calibration procedures, new solutions, new cell preparations, and a new micro lysis-analysis procedure in a critical new sequence of steps to measure cell fragility in microscopic regions of a cell-containing micro-sample.

Accordingly, it is an object of the present invention to utilize a generally known configuration of microscope, light source, light control, television imaging, and video recording equipment to provide microscopic images of cell samples.

It is a further object of the present invention to provide a new microscope calibration procedure to provide exposures of cells to quantitated, focused, frequency-specific energies.

It is a further object of the present invention to utilize a generally known selection procedure to obtain a cell specimen.

It is a further object of the present invention to utilize preparation of a standard buffer solution to provide a standardized environment for the cell specimen.

It is another object of the present invention to provide a new method for a quantifiable cell-attack agent in different microscopic areas of micro-samples of the cell specimen.

It is yet another object of the present invention to provide a new method for preparation of the cell specimen to give a standardized mixture of cells and a cell-attack agent in a standardized solution (buffer) environment.

It is a further object of the present invention to provide a new micro-sample preparation for subsequent measurements of cell rupture.

It is a further object of the present invention to provide a new micro-lysis procedure for precision energy activated cell-attack to rupture the cells in the micro-sample in a new standardized manner.

It is yet a further object of the present invention to provide a new procedure for micro-analysis of micro-sample images to measure the time-sequenced rupture of cells during energy-activated cell-attack in microscopic regions of the micro-sample.

These and other improvements will be better understood on reading the description which follows.

BRIEF DESCRIPTION OF THE DRAWINGS

A better understanding of the present invention will be had upon reference to the following description in conjunction with the accompanying drawings, wherein:

FIG. 3 is a plot showing a repeat of the curve (open circles) of FIG. 1 as the graphical basis for definition of:

1) the Maximal Micro-lysis Response (MR) as the zero-time Response-Area Optical Density (ZROD) minus the Minimum Plateau Response-Area Optical Density (PROD);
2) the Percent Maximal Response (MR%) as 100 times MR divided by ZROD; and
3) the % Response at a specific time t (% Response (t)) as 100 times the quantity, ZROD minus the Response-Area Optical Density at time t (ROD(t)), that resultant quantity divided by MR.

Figure 1:
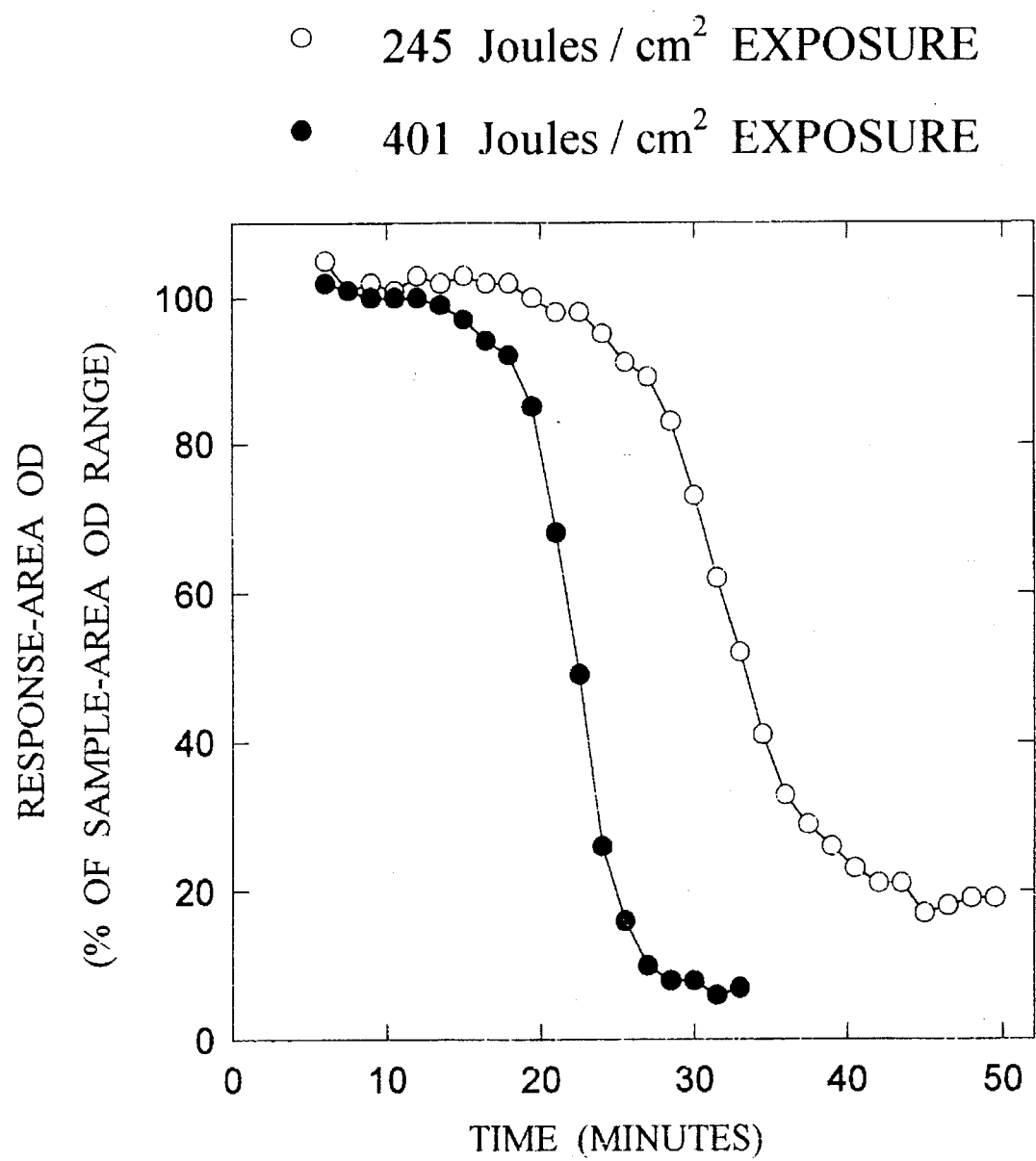
FIG. 1 is a plot showing curves for the percentage number of surviving intact human red blood cells (measured as a relative Response-Area Optical Density) in two rectangular microscopic areas of a cell micro-sample as a function of time from the beginning of a second-energy exposure of 245 Joules/cm$^2$ (open circles) which activates the cell-attack agent to a low degree in one rectangular microscopic area to create a moderate rate of micro-lysis over a 40–50 minute period in that area of the micro-sample and a second-energy exposure of 401 Joules/cm$^2$ (filled circles) which activates the cell-attack agent to a higher degree in a second rectangular microscopic area to create a higher rate of micro-lysis over a 25–30 minute period in that second area of the micro-sample.
Figure 2:
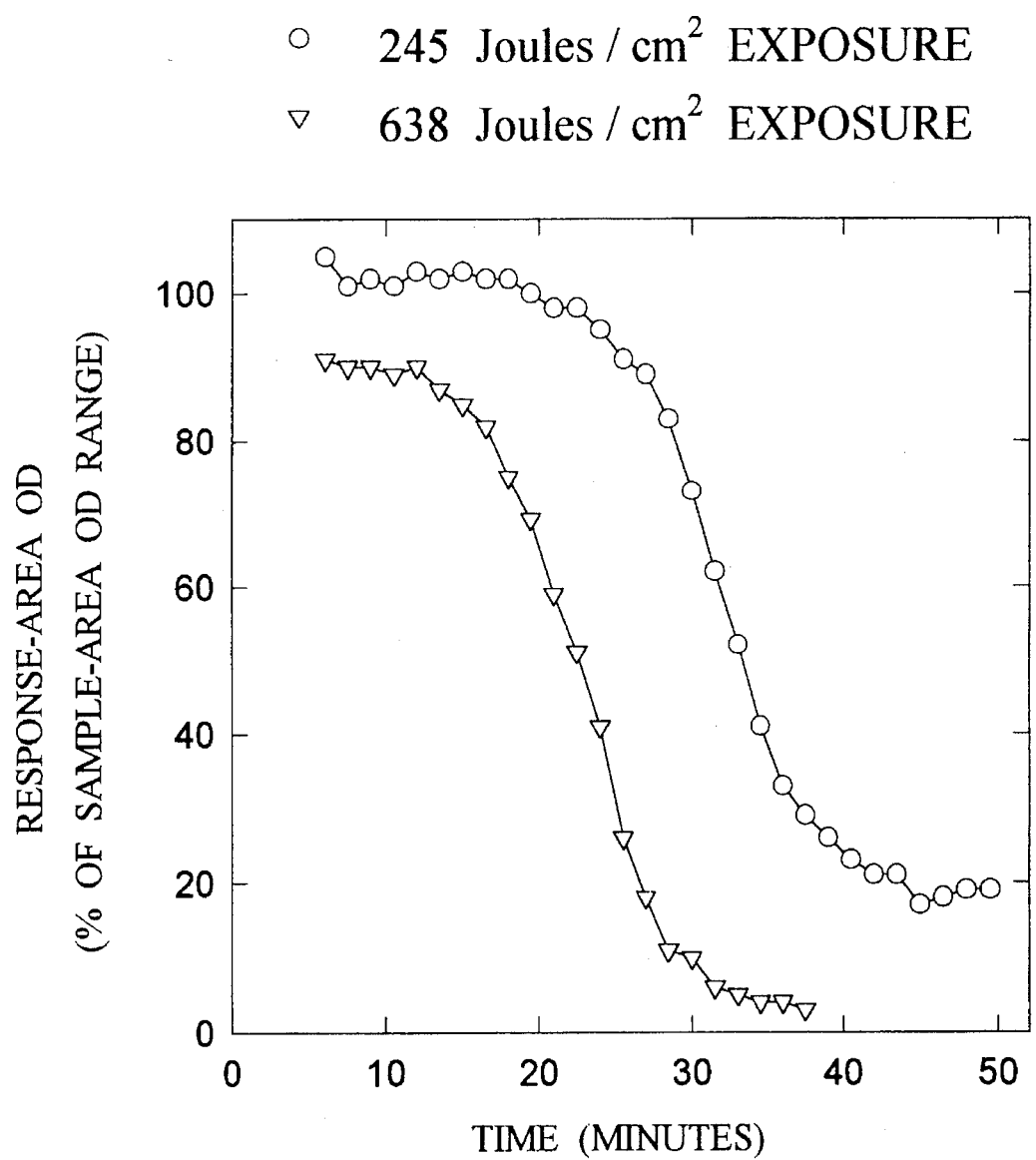
FIG. 2 is a plot showing a repeat of the micro-lysis curve (open circles) of FIG. 1 for second-energy cell-attack activation at 245 Joules/cm$^2$ in one rectangular microscopic area of the cell micro-sample and gives a Response-Area Optical Density curve as a function of time from the beginning of a second-energy cell-attack activation of 638 Joules/cm$^2$ (filled circles) to create micro-lysis in a third rectangular microscopic area of the micro-sample that gave FIG. 1.
Figure 3:
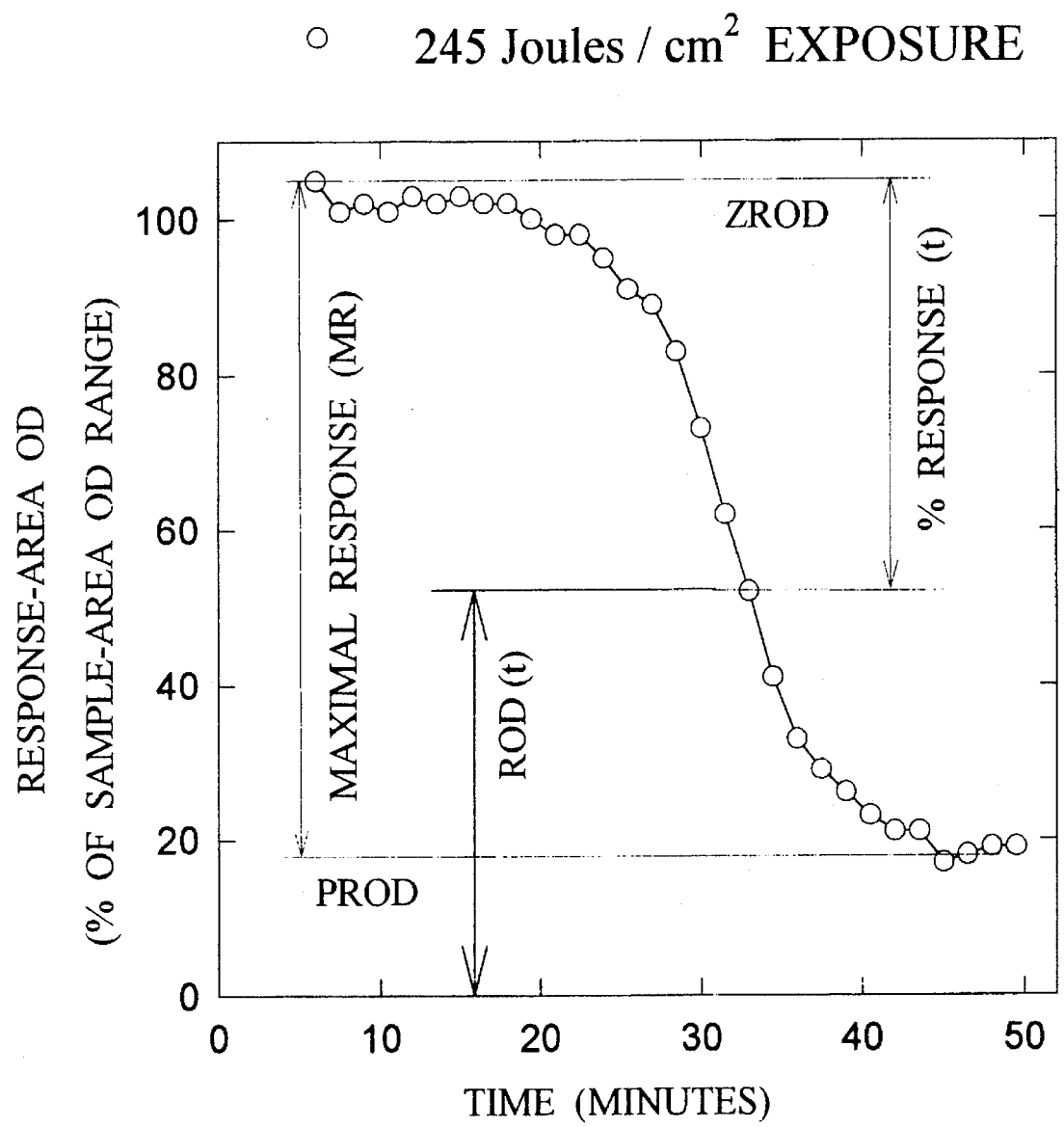
Figure 4:
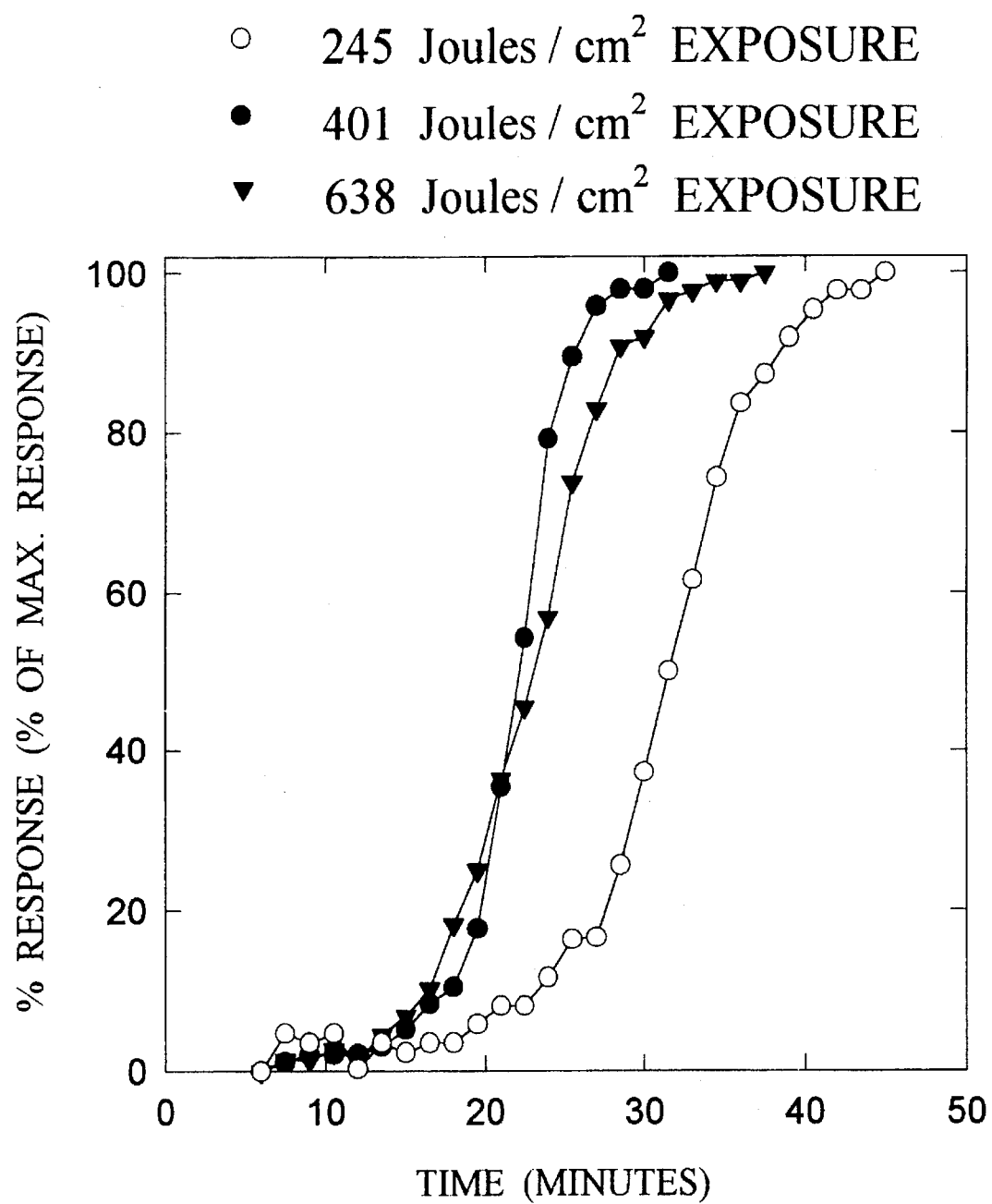

FIG. 4 is a plot showing the three micro-lysis % Response curves which are generated by application of the definitions in FIG. 3 to the three Response-Area Optical Density curves in FIG. 1 and FIG. 2.

Figure 5:
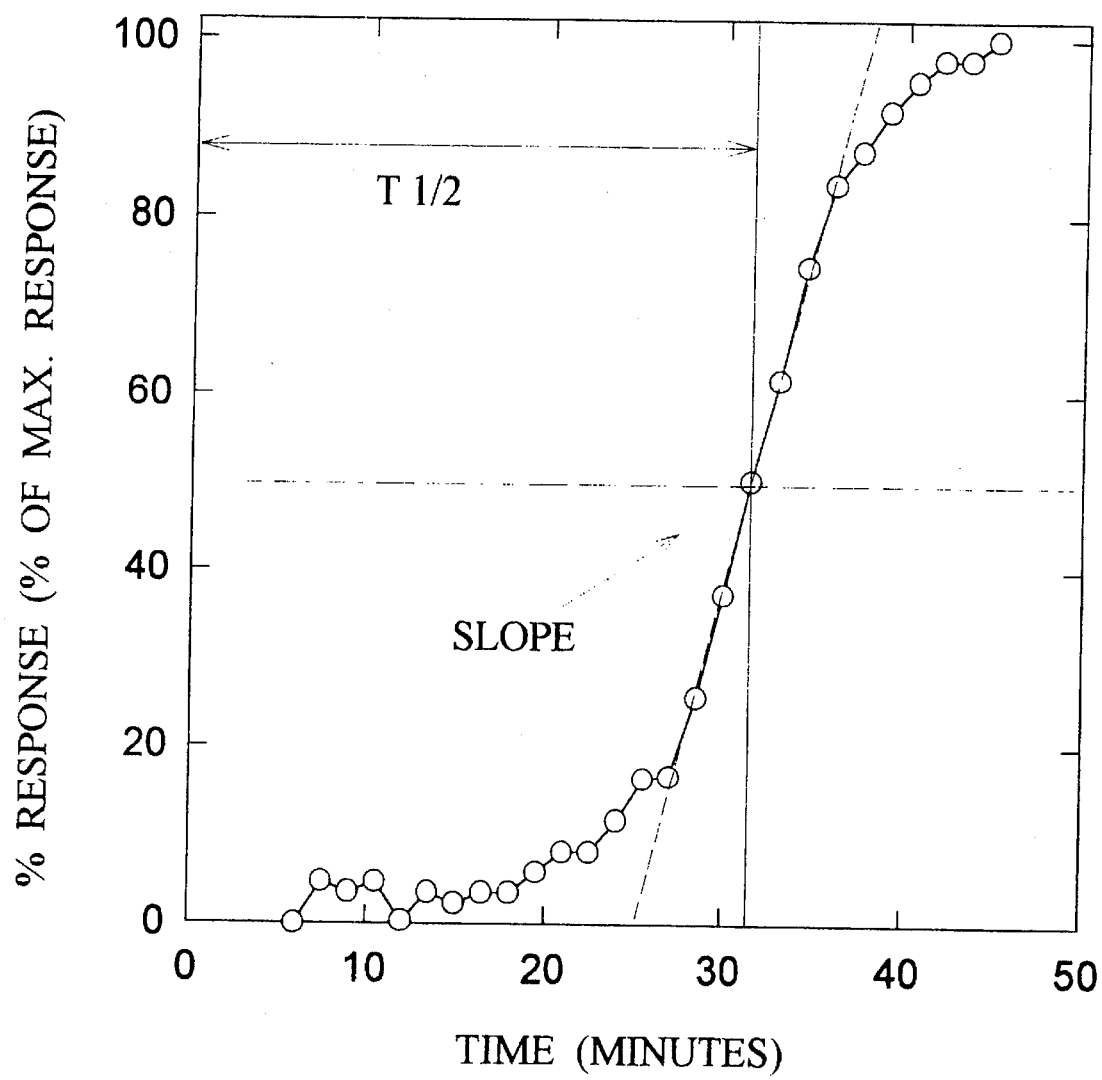

FIG. 5 is a plot showing a repeat of the micro-lysis % Response curve (open circles) of FIG. 4 as the graphical basis for definition of:

1) the response half-time ($T_{1/2}$) as the period from the beginning of cell-attack activation to the time of the 50-percent response value, and
2) the largest slope of the % Response Curve as the Slope at time $t=T_{1/2}$.

Figure 6:
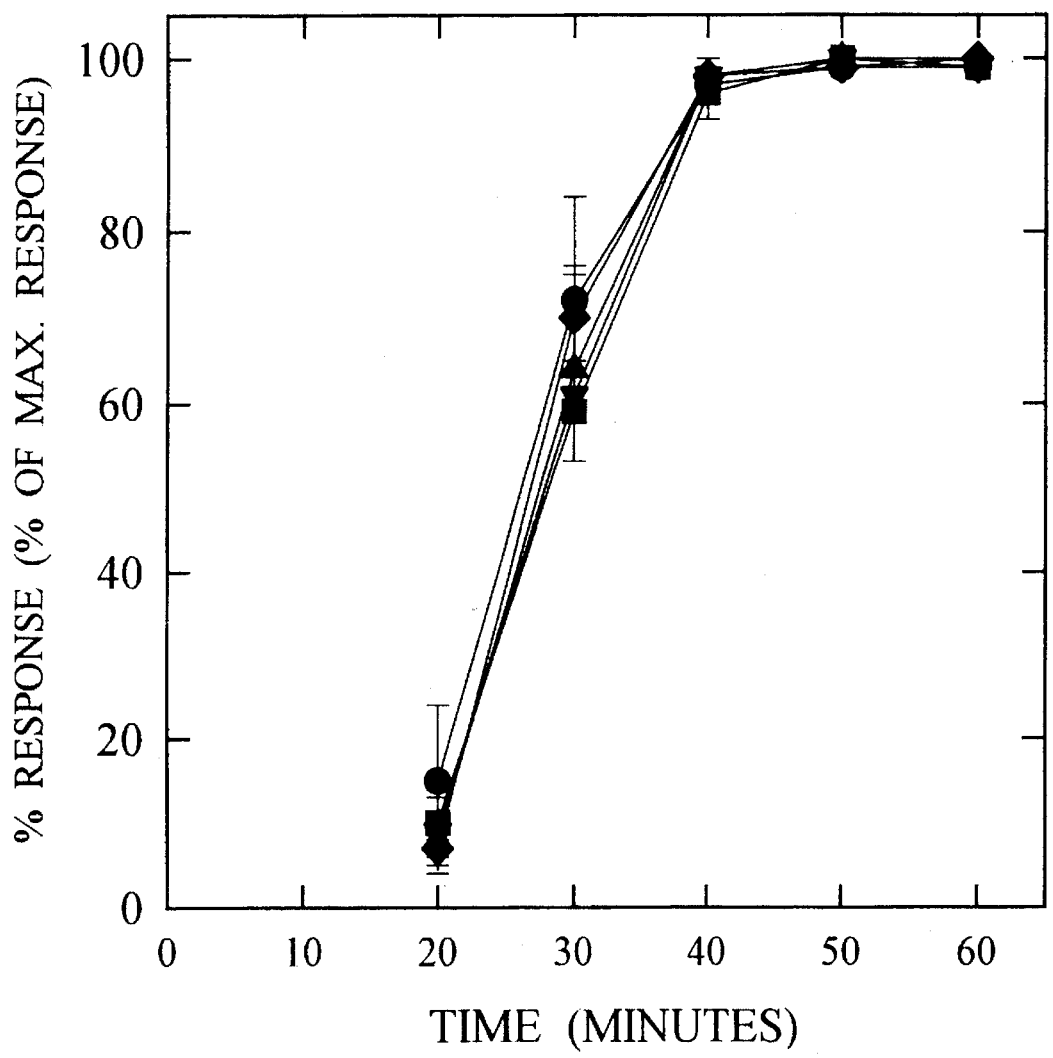

FIG. 6 is a plot showing the % Response curve (mean±SEM) for micro-lysis on day 1 at 7 hours (circles), day 2 (squares), day 3 (triangles), day 4 (diamonds), and day 5 (inverted triangles) after collection of red blood cells from four rabbits.

Figure 7:
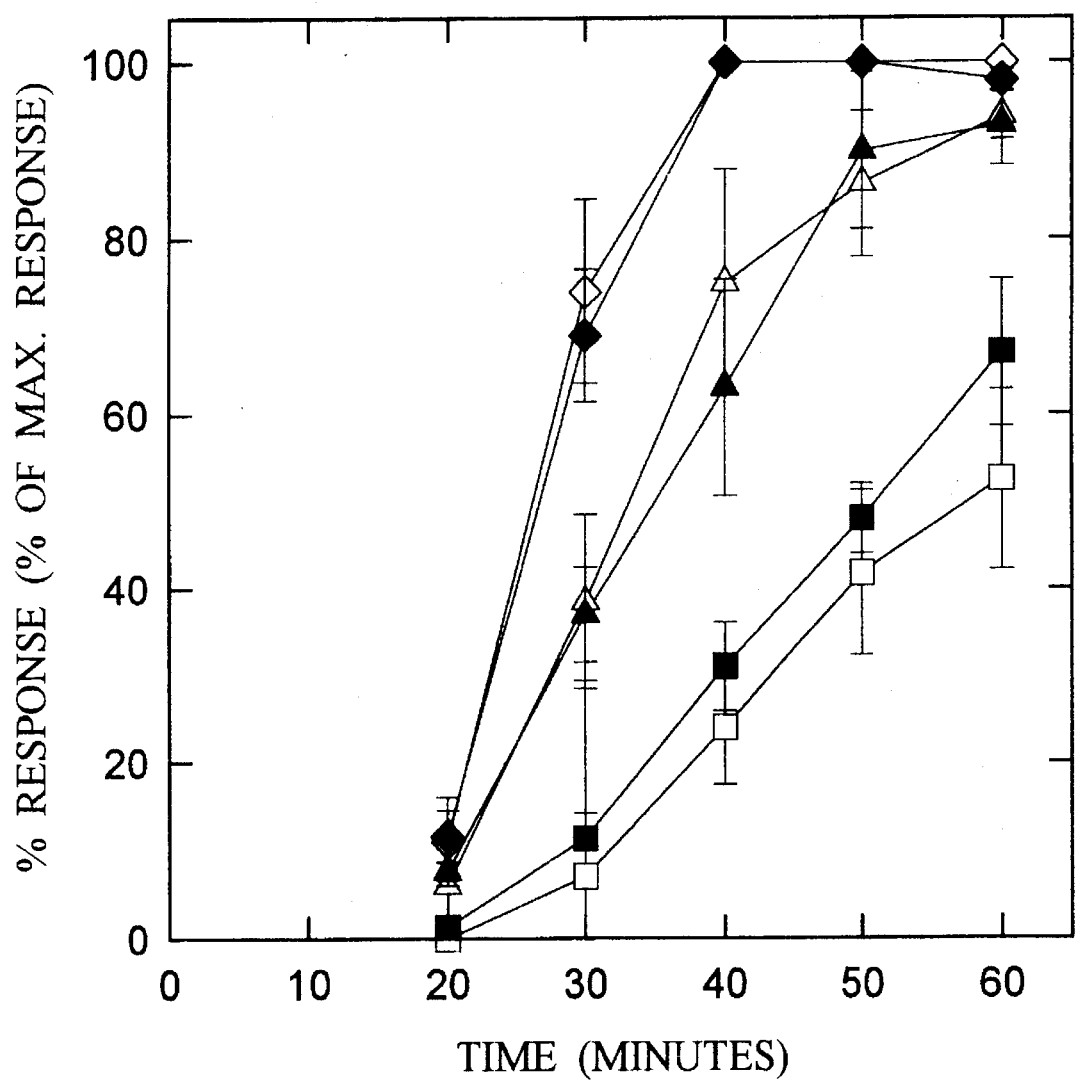

FIG. 7 is a plot showing the % Response curves (mean±SEM) for the effect of cell-attack activation of 105 Joules/cm$^2$ (open squares), 126 Joules/cm$^2$ (filled squares), 159 Joules/cm$^2$ (open triangles), 168 J/cm$^2$ (filled triangles), 210 J/cm$^2$ (open diamonds), and 210 J/cm$^2$ (filled diamonds) on rabbit (N=3) red blood cells.

Figure 8:
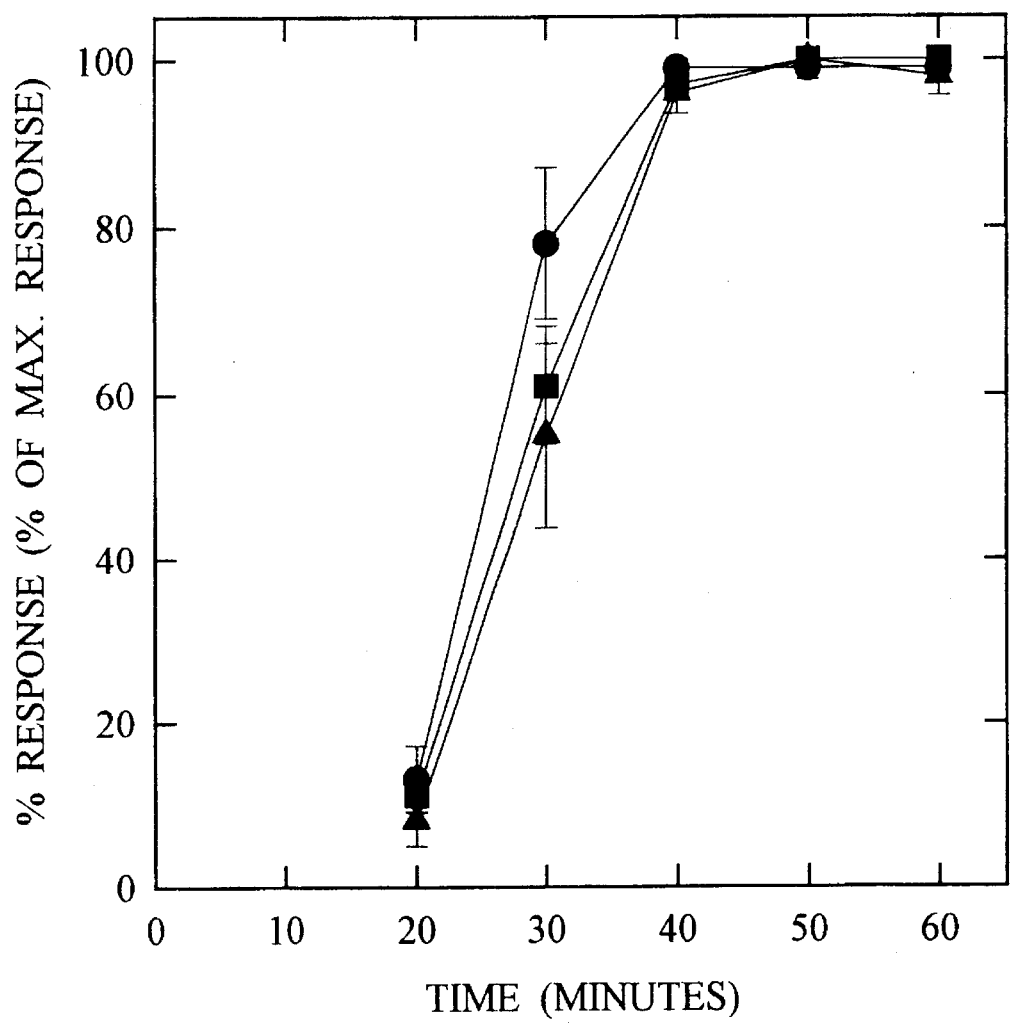

FIG. 8 is a plot showing the % Response Curves (mean±SEM) for micro-lysis of 3% (circles), 4% (triangles), and 5% (squares) concentrations of rabbit (N=4) red blood cells.

Figure 9:
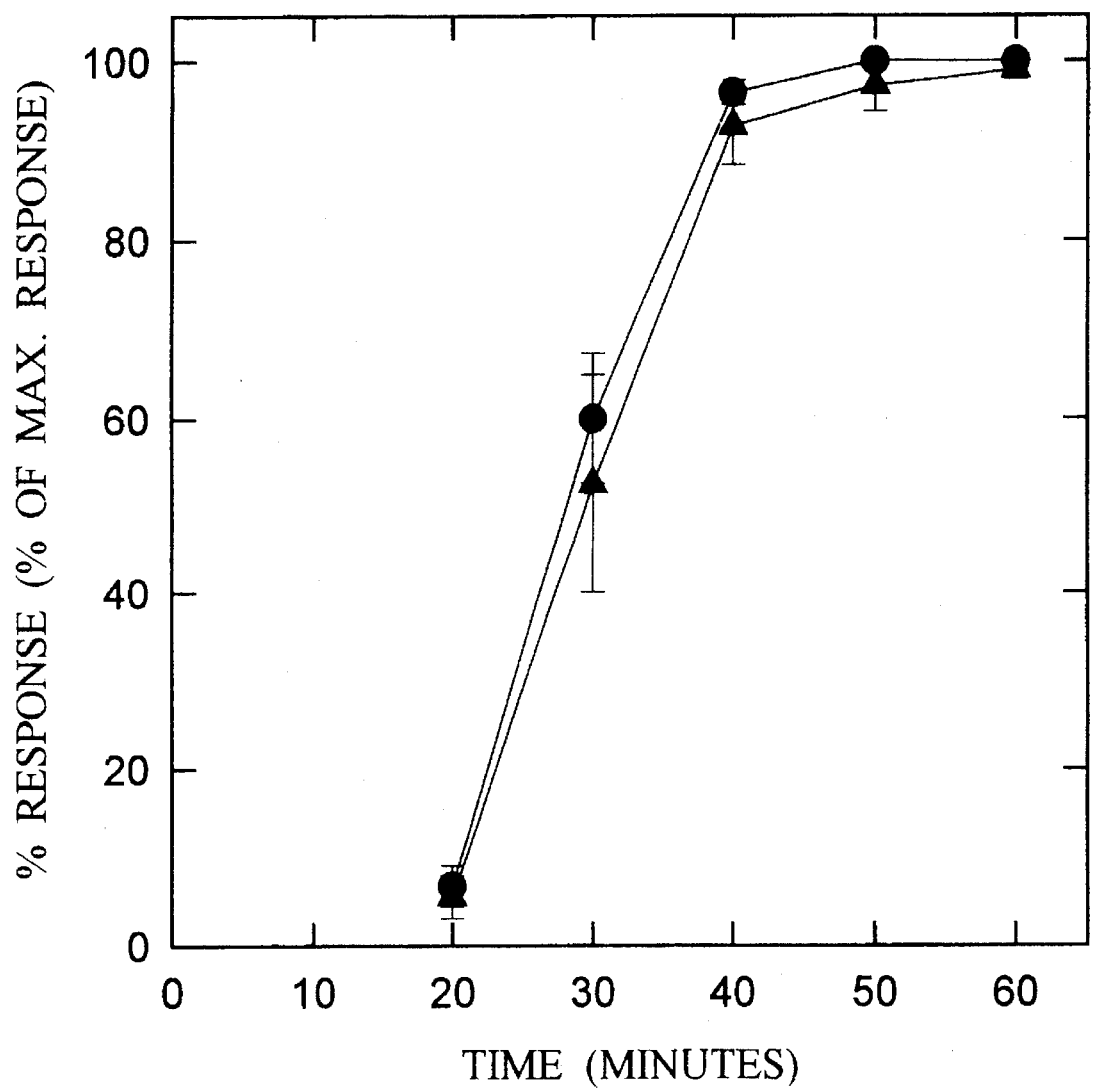

FIG. 9 is a plot showing the % Response curves (mean±SEM) for micro-lysis of rabbit (N=3) red blood cells that had been separated from whole blood (circles) and for red blood cells in whole blood that contained plasma and other cells such as platelets and white blood cells (triangles).

Figure 10:
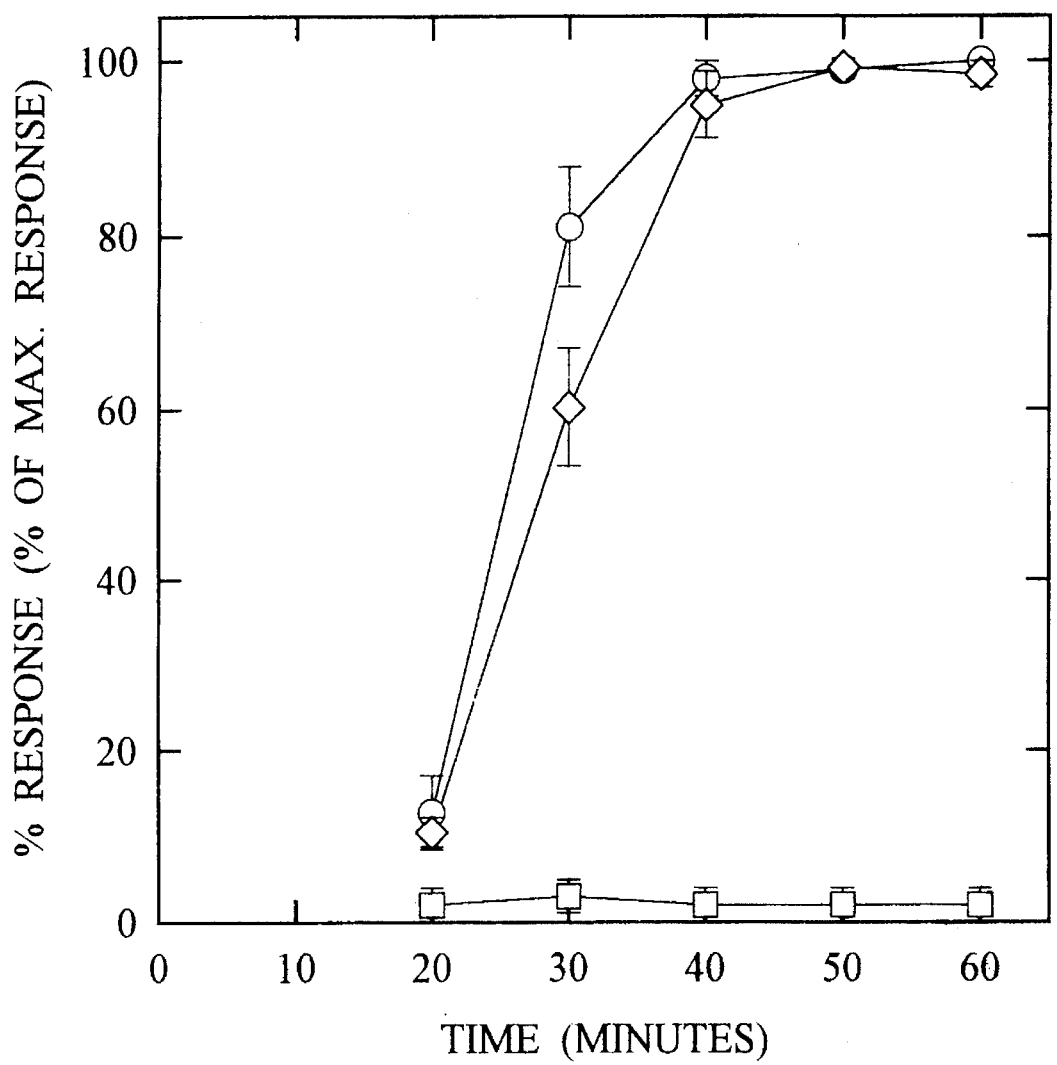

FIG. 10 is a plot showing the % Response curves (mean±SEM) for micro-lysis of rabbit (N=4) red blood cells on day 5 (circles), on day 5 after the red blood cells had been washed and reconstituted with buffer and the cell-attack agent FITC-dextran (diamonds), and on day 5 after the red blood cells had been washed and reconstituted with buffer but not the cell-attack agent FITC-dextran (squares).

Figure 11:
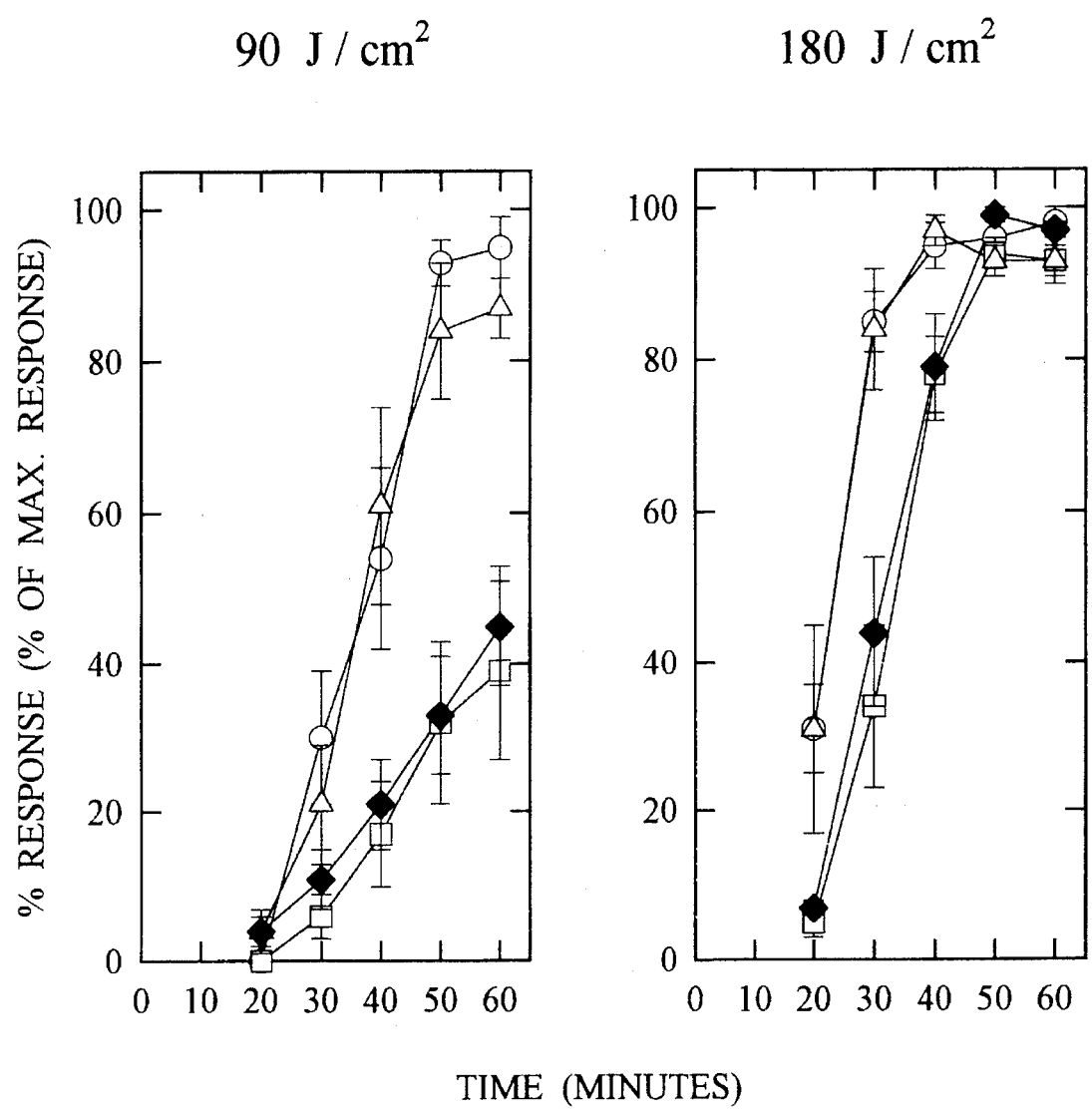

FIG. 11 is a plot showing the % Response curves (mean±SEM) for micro-lysis of rabbit (N=4) red blood cells that had been prepared in standard buffer with glucose and albumin (squares), buffer with glucose but not albumin (filled diamonds), buffer with albumin but not glucose (triangles), and buffer without albumin and glucose (circles).

Figure 12:
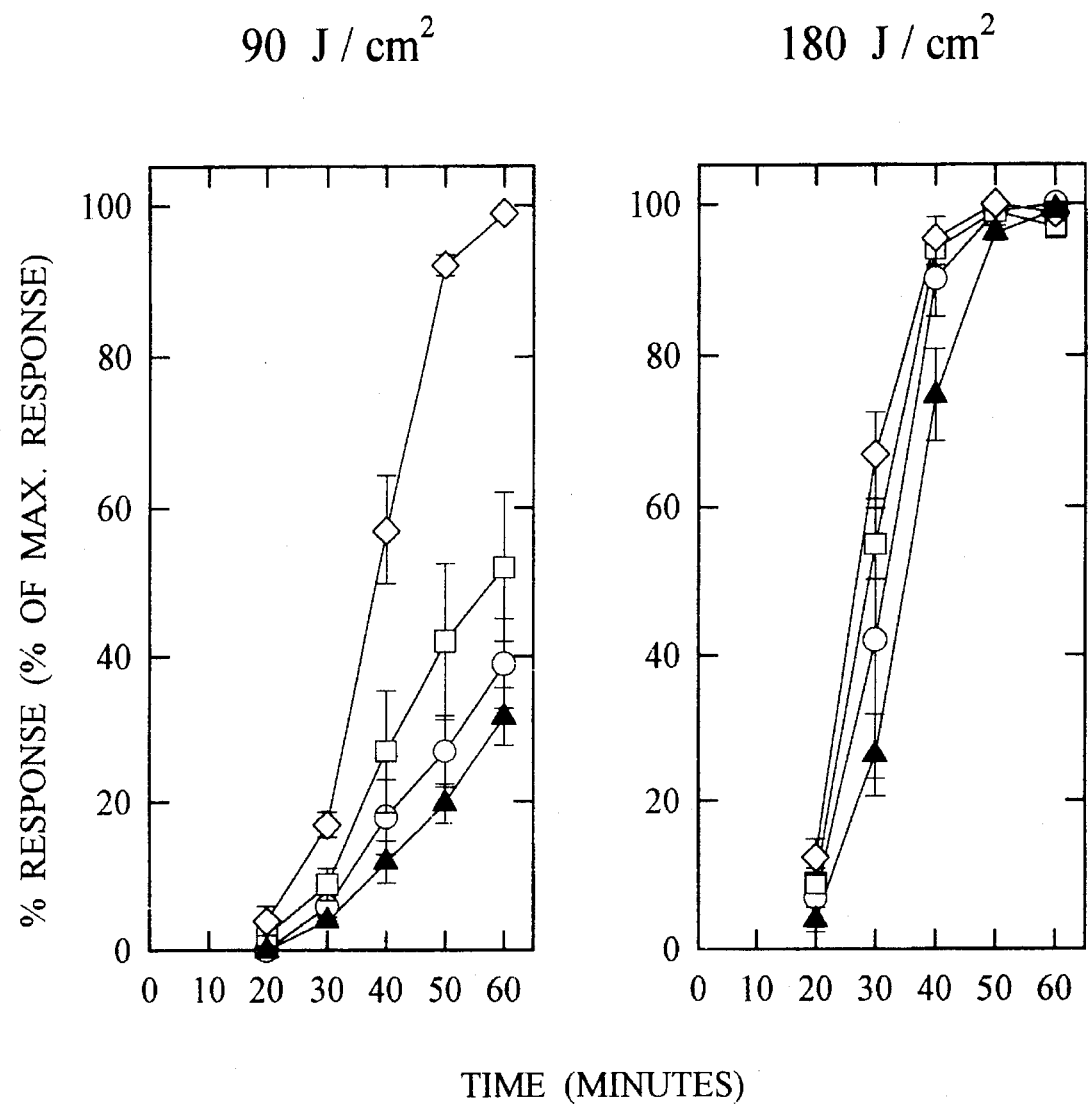

FIG. 12 is a plot showing the % Response curves (mean±SEM) for micro-lysis of rabbit (N=6) red blood cells which had been previously incubated for one hour with a test chemical diamide at a concentration of 5.0 milliMolar (diamonds), 0.5 mM (squares), 0.05 mM (circles), or 0.00 mM (filled triangles), with cell-attack activations of 180 J/cm$^2$ (right panel) and 90 J/cm$^2$ (left panel).

Figure 13:
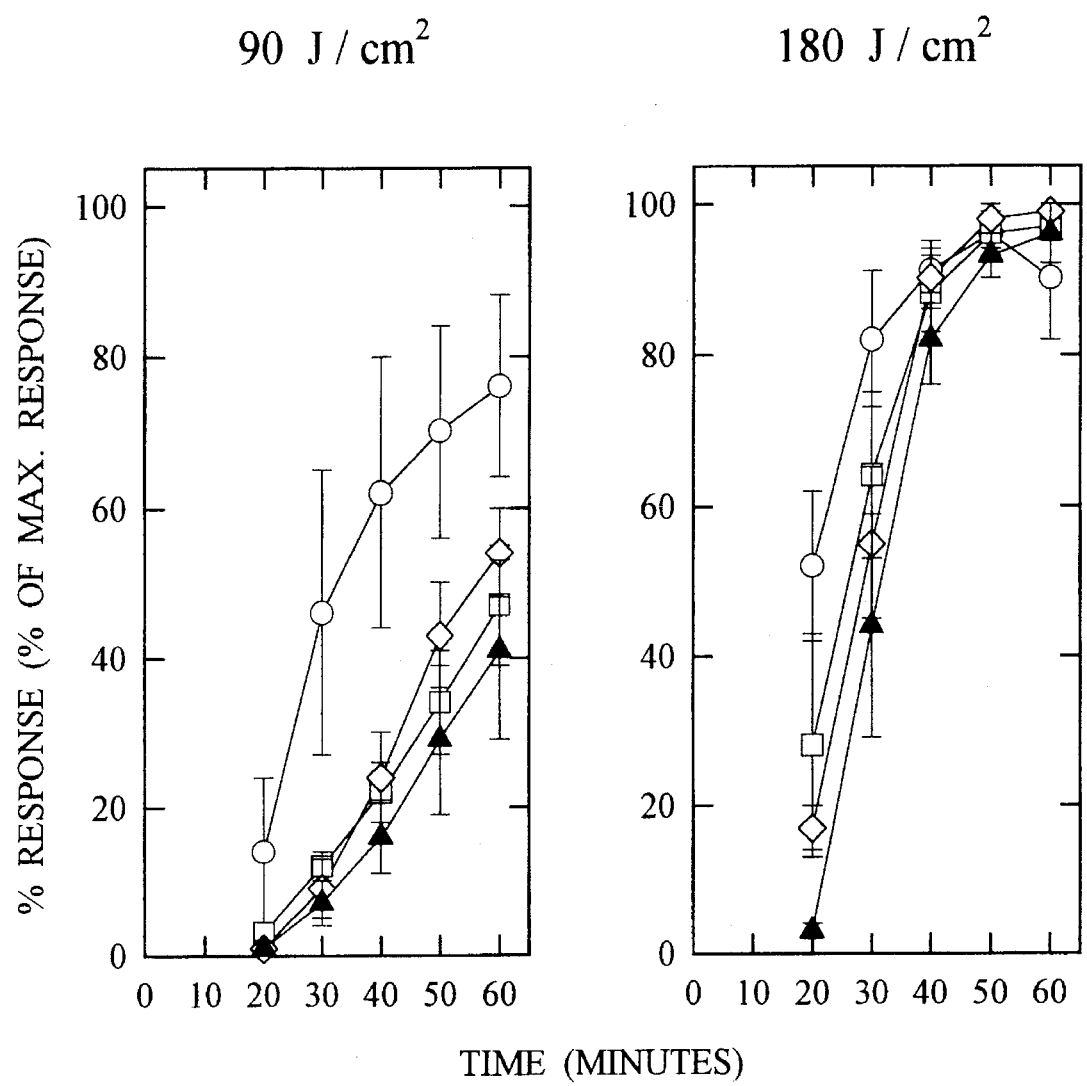

FIG. 13 is a plot showing the % Response curves (mean±SEM) for micro-lysis of rabbit (N=5) red blood cells which had been previously incubated for 20 minutes with the anesthetic Chlorpromazine at a concentration of 100 microMolar (circles), 30 μM (diamonds), 10 μM (squares), and 0 μM (filled triangles), with cell-attack activations of 180 J/cm$^2$ (right panel) and 90 J/cm$^2$ (left panel).

Figure 14:
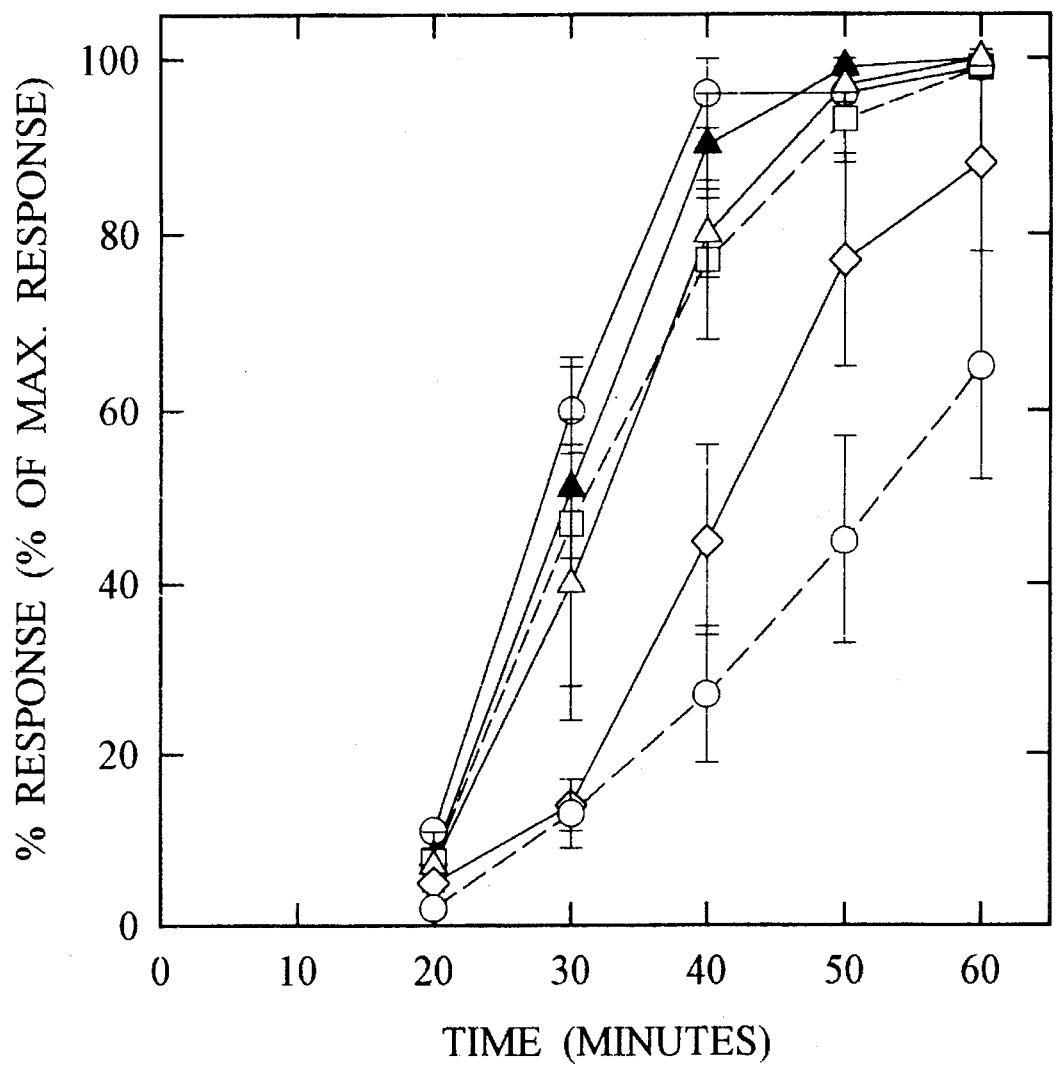

FIG. 14 is a plot showing the % Response curves (mean±SEM) for micro-lysis of rabbit (N=6) red blood cells which had been previously incubated for one hour with the test chemical glutaraldehyde at a concentration of 0.02% (circles with dashed line), 0.01%, (diamonds), 0.005% (triangles), 0.0025% (squares with dashed line), 0.00125% (circles), and 0.000% (filled triangles).

Figure 15:
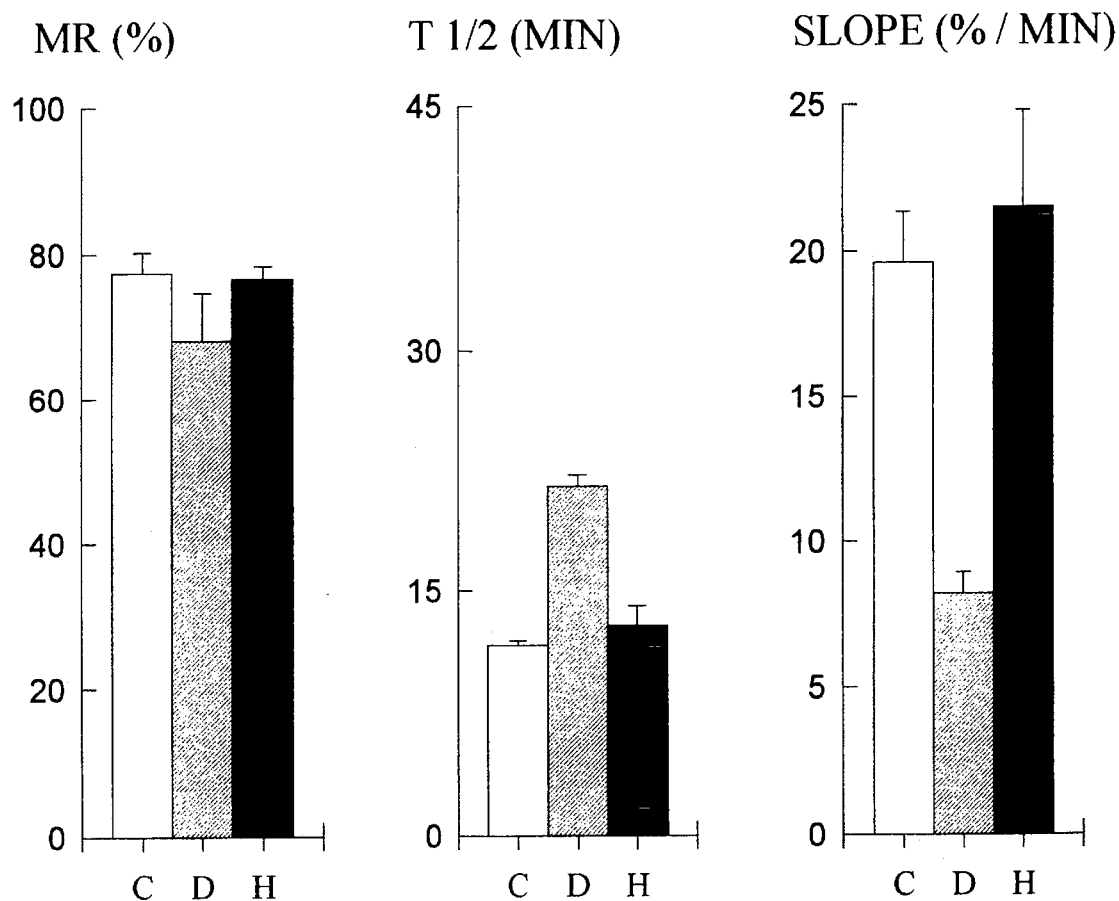

FIG. 15 is a bar graph showing the Percent Maximal Response (MR%) and the $T_{1/2}$ and Slope values of the % Response curves for micro-lysis of red blood cells from 5 normal control Sprague-Dawley laboratory rats (C) at the cell-attack activation of 248±3.6 J/cm$^2$, 3 streptozoticin-induced insulin-dependent diabetic Sprague-Dawley rats (D) at 245±4.1 J/cm$^2$, and 6 diet-induced hypercholesterolemic Sprague-Dawley rats (H) at 249±2.7 J/cm$^2$.

Figure 16:
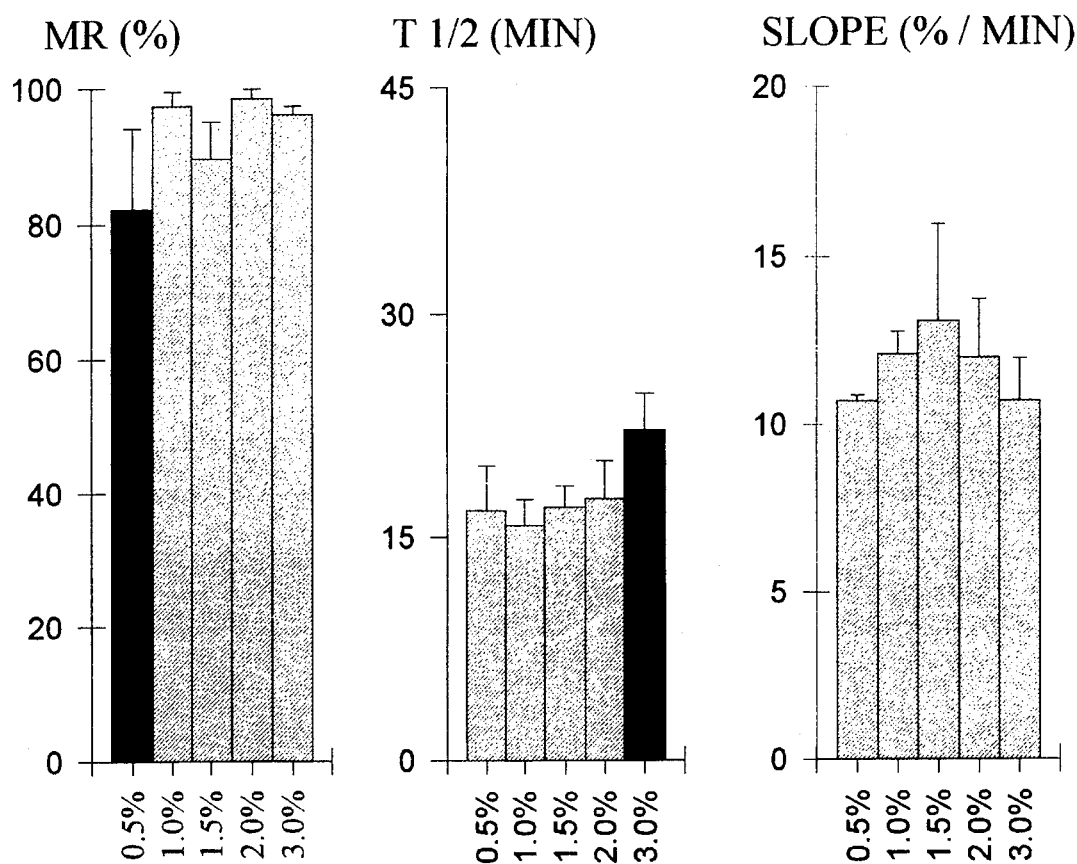

FIG. 16 is a bar graph showing the Percent Maximal Response (MR%) and the $T_{1/2}$ and Slope values of the % Response curves for micro-lysis of 0.5% to 3.0% concentrations of human (N=3) red blood cells. One subject received a Cell-attack activation of 549±0.3 J/cm$^2$, the second subject received 340±1.1 J/cm$^2$, and the third subject received 198±1.3 J/cm$^2$ for all five cell concentrations.

Figure 17:
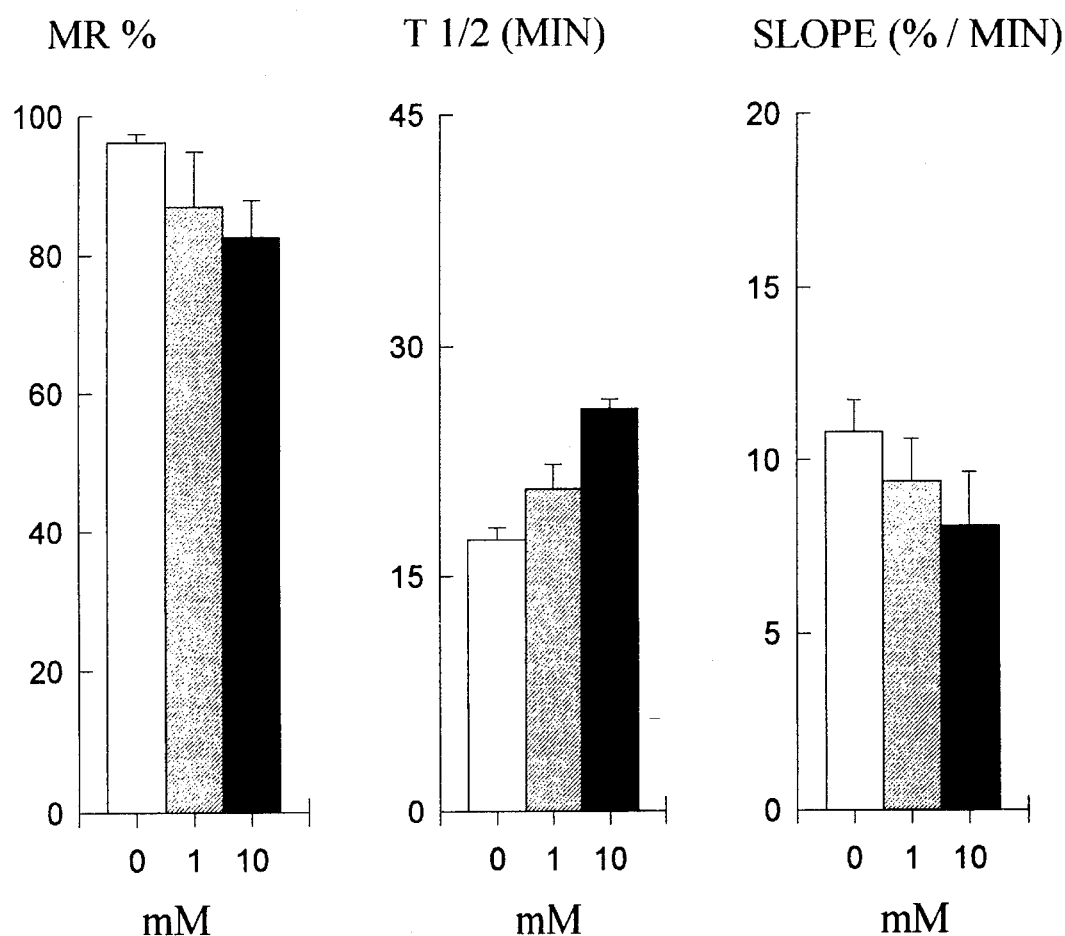

FIG. 17 is a bar graph showing the Percent Maximal Response (MR%) and the $T_{1/2}$ and Slope values of the % Response curves for micro-lysis of human (N=5) red blood cells which had been previously incubated at 4° C. FOR ONE HOUR with the therapeutic drug pentoxifylline (PTFX) at concentrations of 10 milliMolar (filled bars), 1 mM (striped bars), and 0 mM (clear bars). One subject received a cell-attack activation of 658±6.6 J/cm$^2$, three subjects received 329±1.9 J/cm$^2$, and one subject received 196±0.7 J/cm$^2$ for all three pentoxifylline concentrations.

Figure 18:
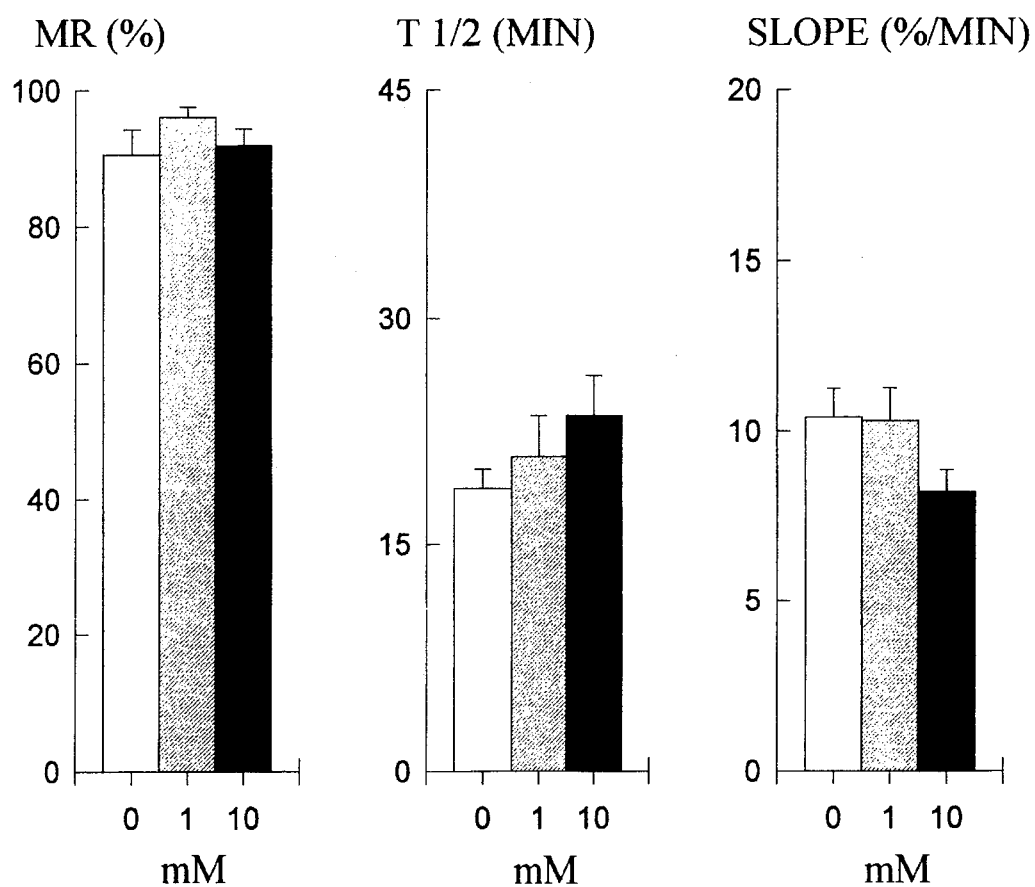

FIG. 18 is a bar graph showing the Percent Maximal Response (MR%) and the $T_{1/2}$ and Slope values of the % Response curves for micro-lysis of human (N=5) red blood cells which had been previously incubated at 4° C. FOR TWENTY-FOUR HOURS with the therapeutic drug pentoxifylline (PTFX) at concentrations of 10 milliMolar (filled bars), 1 mM (striped bars), and 0 mM (clear bars). One subject received a cell-attack activation of 641±3.3 J/cm$^2$, three subjects received 330±1.7 J/cm$^2$, and one subject received 205±0.7 J/cm$^2$ for all three pentoxifylline concentrations.

Figure 19:
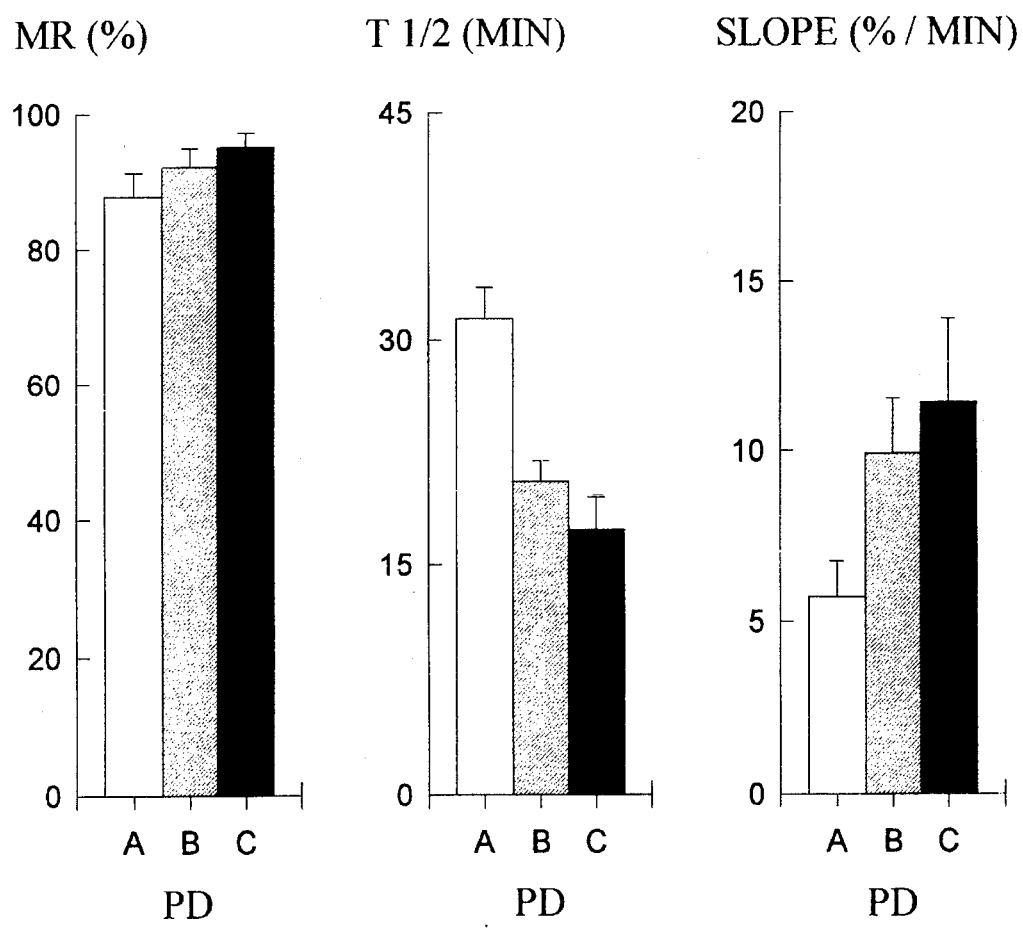

FIG. 19 is a bar graph showing the Percent Maximal Response (MR%) and the $T_{1/2}$ and Slope values of the % Response curves at cell-attack activations of A=243±2.9 J/cm$^2$ (clear bars), B=400±3.6 J/cm$^2$ (striped bars), and C=642±4.0 J/cm$^2$ (filled bars) for micro-lysis of red blood cells from four female and three male African-Americans who had no clinical indicators of sickle-cell disease.

Figure 20:
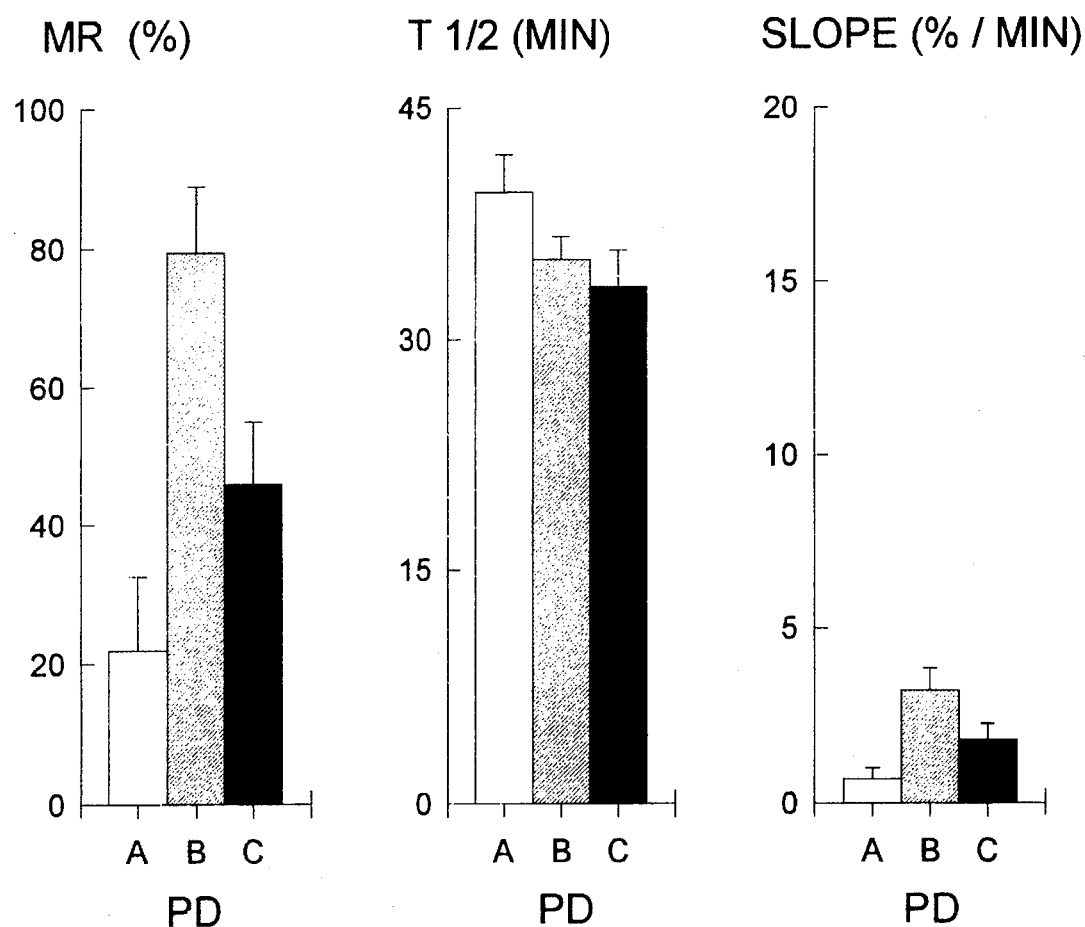

FIG. 20 is a bar graph showing the Percent Maximal Response (MR%) and the $T_{1/2}$ and Slope values of the % Response curves at cell-attack activations of A=247±1.1

J/cm² (clear bars), B=395±5.5 J/cm² (striped bars), and C=643±4.0 J/cm² (filled bars) for micro-lysis of red blood cells from 2 female and 3 male African-Americans with clinical diagnosis of sickle-cell disease but not hemoglobin-F abnormality.

Figure 21:
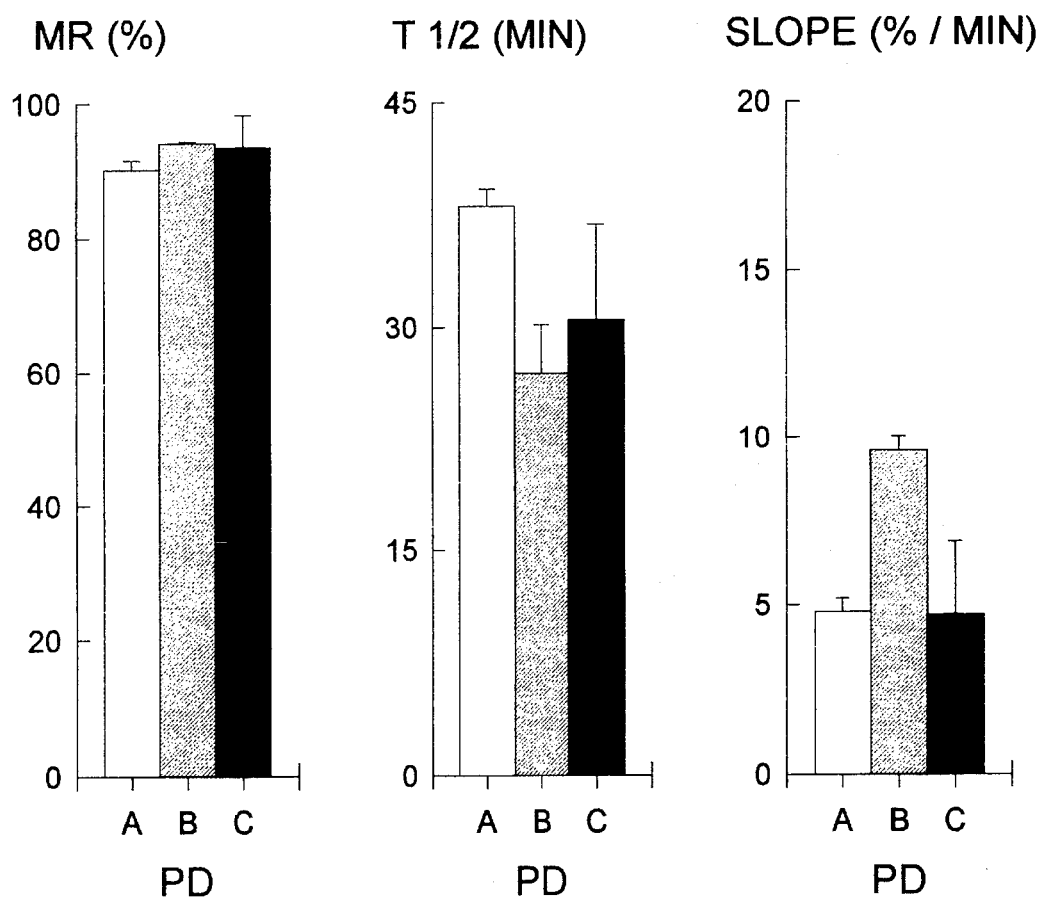

FIG. 21 is a bar graph showing the Percent Maximal Response (MR%) and the $T_{1/2}$ and Slope values of the % Response curves at cell-attack activations of A=253±2.8 J/cm² (clear bars), B=399±4.6 J/cm² (striped bars), and C=661±2.1 J/cm² (filled bars) for micro-lysis of red blood cells from 1 female and 1 male African-American with clinical diagnosis of sickle-cell disease and hemoglobin-F abnormality.

Figure 22:
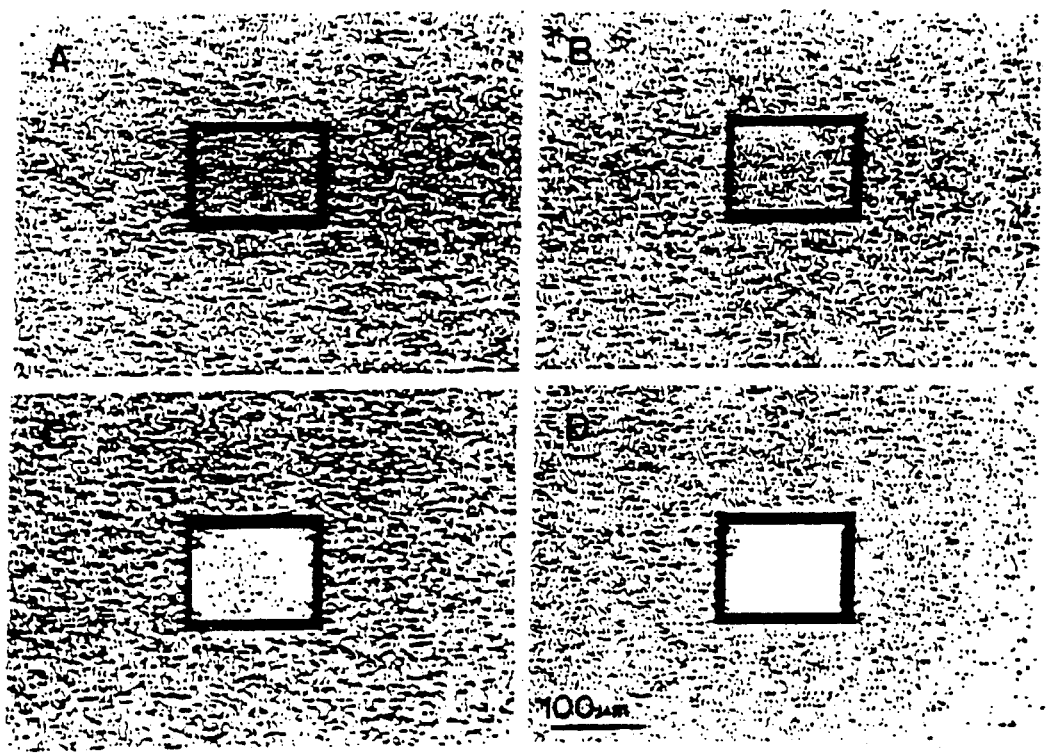

FIG. 22 is a photomicrograph showing the rectangular microscopic area of cell-attack for a cell micro-sample before cell-attack activation as seen in the top left panel, 20 minutes after the start of cell-attack activation as seen in the top right panel, 40 minutes after the start of cell-attack activation as seen in the bottom left panel, and 60 minutes after the start of cell-attack activation as seen in the bottom right panel.

DESCRIPTION OF THE PREFERRED EMBODIMENTS

Process Requirements

The present invention is a process that requires, as a minimum, a micro-sample which contains, as a minimum, the cells of interest and a chemical agent that can be energy-activated to become a cell-attack agent; a device to hold the microsample; a device to focus energy precisely on selected microscopic areas of the micro-sample; a device to produce a first-energy form which is used for the analysis of cell rupture in the selected microscopic areas of the micro-sample; a device to produce a second-energy form which is used to energy-activate the cell-attack agent in the micro-sample; a method to ensure the delivery of a precise amount of the first-energy form to the micro-sample; a method to ensure the delivery of a precise amount of the second-energy form to the micro-sample; a device to measure the amount of the first-energy form that is transmitted through or is reflected from or is scattered from the micro-sample as a function of time; and a method to quantitate the effect of the time-dependent transmitted, reflected, or scattered first-energy measurement of cell rupture in the micro-sample in relationship to the time-dependent amount of the second-energy form that is delivered to the micro-sample.

A number of currently known chemicals are capable of energy activation to become cell-attack agents. It is contemplated that many more such chemicals will be identified in the future. Each known chemical requires energy activation in a specific energy band (i.e. a specific frequency and quantity of energy) to become an effective cell-attack agent. It is contemplated that future such chemicals will be identified to have specific energy bands across a broad range of the overall energy spectrum. The second energy form to be used in the present invention is dependent on the chemical that is selected to be the cell-attack agent in each application of the present invention.

Likewise, each currently known type of cell has a specific energy band (i.e. a specific frequency) in which each respective cell type absorbs, reflects, or fluoresces that energy. It is contemplated that future cell types will be identified to have specific energy bands across a broad range of the overall energy spectrum. The first-energy form to be used in the present invention is dependent on the cell type that is selected to be analyzed for cell fragility in each application of the present invention.

The following elements of the preferred embodiments for the present invention are described for, but are not limited to, a selection of fluorescein isothiocyanate (FITC) as an example of the cell-attack agent and for selection of the red blood cell (erythrocyte) as an example of the cell type. FITC has an absorption energy band centered at approximately 480 nanometers, and the red blood cell has an absorption energy band above 500 nanometers. Both of these absorption bands are in the visible (i.e. light) energy range of the overall energy spectrum. Thus, as a result of those specific selections as examples, the following describes, but is not limited to, a transillumination pathway of a light microscope for the focus of the first-energy form which contains significant energy at energy frequencies above 500 nanometers to be absorbed by the red blood cell as a selected cell type; an epi-illumination pathway of the same microscope for the focus of the second-energy form which contains significant energy at the energy frequency of 480 nanometers to activate FITC as a selected cell-attack agent; and the appropriate energy-measuring equipment for the process to measure energy levels (i.e. quantities) in the visible (i.e. light) energy band at the plane of the micro-sample.

Equipment Configuration

Although any microscope having a 75–300 W arc lamp can be used in the present invention, a Zeiss model 20-T light microscope having a 100 W mercury arc lamp is utilized in the preferred embodiment to provide the second-energy form by epi-illumination of the cell micro-sample through the microscope objective lens. A halogen lamp in the range of 50–300 W, preferably a 100 W halogen lamp, is used to provide the first-energy form by transillumination of the cell micro-sample through the microscope substage condenser. A television camera with external control of target voltage (either a charged-coupled-device (CCD) or a silicon-intensified-target (SIT) camera) is equipped with a microscope eye-piece attachment for adequate microscope-image capture, videorecording, video monitor display, and analysis of micro-lysis. A standard videocassette recorder such as a Panasonic model 6200, a time-date video-insertion generator such as a Panasonic model 810, and a moderate resolution television monitor (at least 600 horizontal lines preferred) are used to record the images of a selected microscopic area of the cell-containing micro-sample for analysis of the first-energy images on-line or off-line at a convenient time.

The preferred embodiment of the present invention uses a light-microscopy objective lens (UMK 50X Leitz) with a 0.60 numerical aperture having a variable built-in lens diaphragm, a microscope tube factor of 1.25 X, an X-Y coordinate movable microscope stage such as that found on a Zeiss 20-T standard microscope, and a brightfield substage condenser such as that found on a Zeiss 20-T standard microscope, all of which are readily available commercial components. A microscope filter cube (Leitz model I-2 preferred) is utilized with a band-pass filter having a preferred range of 450–490 nm, a dichroic mirror preferably with a transmission above 510 nm, and a long-pass barrier filter preferably with a transmission above 515 nm which are chosen to correspond to the absorption and emission frequencies of the chosen energy-activated cell-attack agent such as FITC.

The second-energy form is provided by an epi-illumination pathway through the microscope. This epi-illumination pathway has provisions for the positioning of a variable circular diaphragm, a fixed rectangular diaphragm (4.0×3.5 millimeter aperture preferred), and a neutral density filter carrier between the epi-illumination second-energy source and the microscope filter cube to permit graded and known decreases in the amount of activation energy which impinges as a second-energy form at the cell micro-sample on the microscope stage.

The first-energy form is provided by a transillumination pathway through the cell micro-sample. This transillumination pathway has provisions for the positioning of a circular field diaphragm (22 mm diameter aperture preferred), a circular field energy-limiter (7.5 mm diameter aperture preferred), and a color filter (green preferred for red blood cells) between the transillumination first-energy source and the substage microscope condenser to permit and control the amount of the first-energy form which impinges at the cell micro-sample on the microscope stage.

Microscope Calibration Procedure

The present invention includes a new microscope energy-calibration procedure to provide micro-sample exposures to specific amounts of frequency-specific energies which are quantitated as "energy power" multiplied by the "time of energy exposure." In the following procedure, the critical steps are the independent adjustments of the epi-illumination and transillumination energy pathways to give a specific energy power from each pathway to a specific area at the cell micro-sample when the cell micro-sample is "in focus" on the microscope stage. Energy power at any specific point in an energy path can be measured by any of several instruments (such as an EGG model 580 radiometer). The preferred instrument for energy in the visible energy band is a model 61 United Technology (UT) Optometer which measures energy power in the electrical power equivalents of milliwatts.

To begin calibration of the transillumination pathway, a glass microscope slide is covered with a glass coverslip and is positioned on the stage of the microscope. The epi-illumination pathway is blocked by closure of the variable circular diaphragm. After adjustment of the objective lens to bring the glass slide into focus on the microscope-attached television camera tube, the field diaphragm of the transillumination pathway is adjusted to a nearly closed position (a pin-hole opening) and the substage condenser is raised to bring the pin-hole opening of this field diaphragm into focus. The x-y adjustments of the substage condenser are then used to center the pin-hole opening of this field diaphragm in the microscope field-of-view.

The power supply for the transillumination first-energy pathway is adjusted to approximately 9.2 volts. The energy power for this pathway is measured at the exit of the field energy-limiter, and the field diaphragm is opened until the energy power at the exit of the energy-limiter plateaus to give a value of 1.08 to 1.88 (1.48 preferred) milliwatts. If the plateau energy power is too high or too low at the energy-limiter, the voltage of the first-energy power supply should be adjusted. The energy power is then measured at the glass slide on the microscope stage, and the built-in diaphragm of the substage condenser is partially closed to give 0.044 to 0.052 (0.048 preferred) milliwatts of transilluminated energy power at the glass slide.

To begin calibration of the epi-illumination second-energy pathway, a drop of fluorescein diacetate (1.0 mg/ml concentration) is placed on a glass microscope slide and is covered with a glass coverslip. The slide is placed in a sample carrier which is positioned on the stage of the microscope. The transillumination pathway is blocked by placement of an opaque filter on the field limiter. The variable circular diaphragm of the epi-illumination pathway is slightly opened to focus a fluorescent image of a pin-hole in this diaphragm on the microscope-attached television camera tube. The diaphragm-holder adjustments are used to center the fluorescent image of this circular diaphragm in the television field-of-view.

The circular diaphragm is then opened fully and the fixed rectangular diaphragm is inserted into its carrier in the epi-illumination pathway. The holder adjustments for the rectangular diaphragm are adjusted to center the fluorescent image of this rectangular diaphragm in the television field-of-view. The second-energy source adjustments in the source housing for the epi-illumination second-energy pathway are then used to produce an even fluorescence intensity across the television image of the rectangular diaphragm. The circular diaphragm of the epi-illumination pathway is closed completely and then opened to the point where the rectangular diaphragm is imaged as a uniform fluorescent rectangular area without any reflections of stray energy in the television field-of-view.

The energy power of the epi-illumination second-energy pathway is measured at the focal plane of the objective lens (which corresponds to the position of the coverslip in the sample carrier on the microscope stage when that coverslip is in focus in the television field-of-view), and this energy power is adjusted to a value of 0.39 to 0.41 (0.40 preferred) milliwatts by partial closure of the diaphragm in the objective lens. (If the energy power is too low at this point, the epi-illumination second-energy source has aged and should be replaced.)

Neutral Density (ND) filters are then placed one at a time in the epi-illumination pathway to provide calibration of graduated decreases in the epi-illumination second-energy power at the focal plane of the objective lens. Nominal epi-illumination second-energy power values are 0.30–0.32 milliwatts for an ND of 0.1, 0.18–0.20 milliwatts for an ND of 0.3, and 0.10–0.12 milliwatts for an ND of 0.6.

The amount of epi-illumination, which is the second-energy form used to energy-activate a cell-attack agent to rupture cells in a micro-sample (described below) on the microscope stage, is quantitated as an energy density (ED) which equals epi-illumination energy power at the micro-sample, multiplied by time of epi-illumination energy exposure, divided by the micro-sample area of epi-illumination energy exposure. For the above-described equipment configuration and calibration procedure, the area of epi-illumination energy exposure is determined by the fixed rectangular diaphragm which has a projected image area of 0.000175 cm$^2$ (140.91 µm×124.24 µm) at the focal point of the microscope objective lens.

A common unit for energy density is Joules/cm$^2$ where one Joule equals the total energy that is released in one second by a one-ampere current flowing through a one-ohm resistor (which is electrically equivalent to one watt or 1000 milliwatts of power for one second). For the above-described calibration procedure, the epi-illumination energy power is measured as milliwatts (mw) by the UT Optometer, and epi-illumination exposure time is measured in 0.01 minute increments by the time-date video-insertion generator. The following formula is used to convert these measured units into epi-illumination energy density (ED) for the second-energy form with units of J/cm$^2$ (i.e. Joules÷cm$^2$):

Energy Density=Power×time÷area; or

Joules/cm$^2$=Watts×Seconds÷cm$^2$; or

ED (J/cm$^2$)=(mw÷1000)×(minutes×60)÷(0.000175 cm$^2$); or

ED (J/cm$^2$)=(342.86)×(mw)×(minutes)÷1 cm$^2$.

The above-described calibration procedure gives the following epi-illumination energy densities (ED at the focal point of the microscope objective lens) which result from use of the preferred epi-illumination neutral density (ND) filters:

| ND | POWER (mw) | ED (Joules/cm$^2$) |
|---|---|---|
| 0.0 | 0.40 | 137.14 × exposure mins |
| 0.1 | 0.32 | 109.71 × exposure mins |
| 0.3 | 0.20 | 68.57 × exposure mins |
| 0.6 | 0.10 | 34.29 × exposure mins |

Typical epi-illumination second-energy exposure times are 1 to 10 minutes to give final gradations in the epi-illumination energy density over a range of 34.29 to 1,371.40 J/cm$^2$ which provide gradations in the second-energy activation of the cell-attack agent to rupture cells as different lysis rates in a microscopic area of a micro-sample on the microscope stage.

The last step in microscope calibration is adjustment of the camera target-voltage when the cell micro-sample is first placed on the microscope stage. This adjustment qualitatively positions the camera target-voltage (baseline target current) at approximately the midpoint of the linear voltage range of the camera to give a reasonable picture for the transilluminated first-energy image of the cell micro-sample. Quantitative measurement of this starting camera voltage is not required because subsequent changes in first-energy intensity at the camera target are measured as a percentage change in camera target current, which is independent of the starting target voltage when that target voltage is in the linear voltage range of the camera.

Cell Collection Procedure

Arterial, venous, or mixed capillary (finger stick) blood can be used for micro-lysis of red blood cells. The data in this patent report were obtained from standard venipuncture of the antecubital vein in awake humans and the ear vein of awake New Zealand white rabbits (2.5–4 kg) to collect blood (typically 1–2 ml) into sterile tubes which contained citrate to prevent clotting.

Blood is stored in a 0°–4° C. refrigerator before preparation of blood specimens and cell micro-samples. All cell and solution procedures use only sterile disposable pipette tips, microcentrifuge tubes, bottles, stoppers, and labware to prevent cell contamination and infection.

Buffer Solution Preparation

Subsequent blood dilutions (described below) are done with a typical buffer solution consisting of 7.6 g/l NaCl, 0.26 g/l NaHPO$_4$·H$_2$O, 1.28 g/l Na$_2$HPO$_4$, 4 g/l glucose, and 5 g/l bovine serum albumin. Buffer solution pH is adjusted to 7.4 (normal blood pH) by addition of 1N NaOH. The final osmolality of this buffer solution is 311 mOsm (near normal blood pH). Other buffer solutions can be used; however, glucose and albumin are necessary ingredients to stabilize the cell preparation and to provide restricted-permeability molecules for control of transcellular water movements which can otherwise affect the subsequent micro-lysis process. Likewise, a final osmolality in the range of 295–315 mOsm is critical since overall buffer solution osmolality also affects the rapid phase of transcellular water movements across the cell membrane.

The final step in buffer solution preparation is vacuum aspiration of the buffer solution through a sterile 0.2 micron Nalgene filter to remove any bacteria or other particulate contaminants. The filtered buffer solution is allocated into sterile glass bottles (20 ml preferred) with rubber stoppers for subsequent cell-specimen preparation.

Cell-attack Solution Preparation

The type of energy-activated agent that is used for cell attack is specific to the type of cell to be analyzed, and there is more than one type of cell-attack agent which can be used for any one cell type. For example, phloxine B, eosin-isothiocyanate, pheophorbide, and protoporphyrin have been used by others for photohemolysis of red blood cells in a relatively large-volume cuvette. The preferred cell-attack agent for micro-lysis of red blood cell membranes is fluorescein isothiocyanate (FITC) which is conjugated to a larger macromolecule (20,000 dalton dextran preferred). FITC-dextran is preferred because it does not enter the cell, and there is little blood absorption of the second-energy at the FITC-activation second-energy frequency of 480 nanometers. Thus, the measured second-energy which is projected onto the micro-sample gives a precise amount of activated FITC as a cell-attack agent.

The FITC-dextran is mixed with a 0.9% NaCl solution to give an FITC-dextran concentration of 50 mg/ml. In the subsequent cell micro-sample, the final FITC-dextran concentration in the micro-sample should be in the 2–8 mg/ml range to give the best energy-activated cell-attack stimulus for micro-lysis of red blood cells.

Cell Specimen Preparation

Micro-lysis can be applied to different types of cells, and the cell-separation part of the cell preparation procedure will depend on the cell type. The following describes the procedure for red blood cells.

The refrigerated blood is inverted gently to mix the blood, and is then diluted (1 to 1) with equal parts of the buffer solution. A small amount (80 to 100 μl) of the diluted blood is drawn into a microhematocrit tube which is spun in an IEC MB hematocrit centrifuge at the recommended speed to compact the red blood cells toward one end of the microhematocrit tube. The length of the compacted red blood cells is then measured to give the hematocrit (% cells) of the diluted blood.

The final cell-specimen is a combination of the diluted blood, the cell-attack agent FITC-dextran, a test chemical (if any), and the buffer solution to give a cell-specimen volume of 1 ml with a composition of 0.5 to 6.0% red blood cells, 2.0 to 8.0 mg/ml FITC-dextran, 0 to 10 mg/ml of the test chemical, and the remainder as buffer. As an illustration, a cell specimen with 4 mg/ml of FITC-dextran (which is prepared to beta 50 mg/ml FITC solution as described above), 3% red blood cells (which comes from a diluted blood solution with 25% hematocrit), and 3 mg/ml of a test chemical (which comes as a 20 mg/ml solution) is obtained by mixing 0.08 ml (calculated as 4/50) of the FITC solution, 0.12 ml (calculated as 3/25) of the diluted blood, 0.15 ml (calculated as 3/20) of the test chemical solution, and 0.65 ml (calculated as 1.0−0.08−0.12−0.15) of the buffer solution. Based on this approach, individual or combinations of soluble materials or chemicals can be tested for an effect on cell response to micro-lysis by a standardized energy-activated cell-attack procedure.

Cell Micro-Sample Preparation

Any type of small volume (50 µl or less) chamber of transparent water-impervious material, such as plastic or glass, can be used to give a cell micro-sample on the microscope stage. The crucial aspect is a chamber and filling procedure that prevents micro-sample loss of water (which would change the cell micro-sample constituent concentrations to alter the micro-lysis procedure). The following describes a simple new micro-sample preparation.

A hemacytometer (Neubauer preferred) and cover slip are sterilized in alcohol and air-dried. As a novel approach of the present invention, four Kerr absorbent points (dental cotton sticks for cavity preparations) are placed in a 0.9% NaCl solution to saturate them. A fine forceps is then used to place two saturated Kerr points in each side-well of the hemacytometer, with care to ensure that no Kerr point touches the inside edge of the hemacytometer trough (otherwise, the solution in the Kerr points would dilute the micro-sample constituent concentrations). The saturated Kerr points are a novel approach to provide a "saturated" water vapor pressure to "replace" any potential loss of micro-sample water to the atmosphere by evaporation through the entrance of the hemacytometer chamber.

A small drop-dispenser is used to pick up a solution of 2.5 g/l globulin (made in distilled water), and this solution is applied to coat the coverslip rests of the hemacytometer. The coverslip is placed on the hemacytometer rests and is lightly tapped to seal the coverslip to the globulin-coated hemacytometer rests. This is a novel approach of the present invention to reduce evaporation of water from the cell micro-sample. In the customary approach by others, the coverslip is placed on the hemacytometer rests without use of a sealant. Small irregularities in the "rests" leave small openings between the coverslip and the "rests." The use of a globulin solution in the present invention to seal these small openings is a novel approach to prevent evaporative water loss from the cell micro-sample.

The cell micro-sample solution is gently mixed by inversion of the solution vial. A sterile transfer pipette is used to aspirate the cell micro-sample solution from the vial and to apply 22–25 µl of the solution to the opening of the hemacytometer/coverslip chamber. Capillary action draws the cell micro-sample solution into the hemacytometer chamber (which has a preferred depth of 0.1 mm to standardize the number of cell layers).

The hemacytometer is then placed in a sample carrier which is positioned on the microscope stage. At this point, the transillumination first-energy pathway is opened (by removing the opaque filter from the field limiter) and the cell micro-sample is brought into focus. The television camera target-voltage is adjusted to the midrange (described above in the microscope calibration procedure).

Micro-Lysis Cell-Attack Procedure

The television-microscope images in the following procedure are video recorded for post-procedure analysis. (These images can also be analyzed on-line at the time of the procedure.)

A five-minute waiting period is used for cells to settle in the micro-sample hemacytometer chamber. Room temperature is recorded and hemacytometer temperature is kept at 23.5° to 24.5° C. to minimize Brownian motion of the red blood cells in the cell micro-sample. The cells are brought to focus during a first-energy transillumination to give a control reading of "background first-energy density" for the cell micro-sample. Then, the transillumination pathway is closed by placing the opaque filter on the field limiter.

The time-date video-insertion generator is reset to 0.00 time (in minutes) and is started at the instant that the second-energy epi-illumination pathway is opened (by removing an opaque filter from the epi-illumination pathway). The focus of the fluorescent image is checked and readjusted if necessary. The second-energy epi-illumination is left on for the necessary time (1 to 10 minutes preferred) with a preselected neutral density filter in the epi-illumination pathway to give a desired level of cell-attack activation which is measured as an epi-illumination second-energy density in Joules/cm$^2$ (as described above in the microscope calibration procedure). At the end of the cell-attack activation time, the epi-illumination pathway is closed (by placing the opaque filter in the epi-illumination pathway), and the first-energy transillumination pathway is opened (by removing the opaque filter on the field limiter) to give cell micro-sample images. These cell images are recorded until lysis (rupture of cells) has reached a maximum (less than 5 intact cells remaining in the rectangular epi-illumination area) or 60 minutes has elapsed, whichever occurs first.

At this point, the hemacytometer cell micro-sample is repositioned manually on the microscope stage to give another microscopic area of the micro-sample for application of another cell-attack activation in the second microscopic area. This procedure allows many measurements of micro-lysis at different cell-attack levels (epi-illumination energy densities) on each cell micro-sample. Hemacytometer grid etchings are used to identify the location of each microscopic cell-attack area which prevents inadvertent overlap of cell-attack areas in multiple micro-lysis procedures on the same cell micro-sample.

Micro Analysis Procedure

After the cell micro-sample (in the hemacytometer) has been placed on the microscope stage, there is a five-minute period for cells to settle in the micro-sample chamber. At this point, transillumination with the first-energy source gives a relatively dark speckled-image of the micro-sample in the television field of view. The speckled nature of this image is caused by the presence of red blood cells which absorb at the first-energy frequency, as shown in FIG. 22.

This transillumination first-energy speckled-image area (which is 6 to 10 times larger than the epi-illumination second-energy rectangular diaphragm area) is digitized (Image Technology digitizing board preferred) to give a digital image with 512×512 pixels (1024×1024 would increase analysis precision) with a digital value between 0 and 255 to represent the energy intensity of each image pixel. The mean of ALL pixel values in this speckled first-energy image is calculated as a micro-sample "background first-energy intensity (BFEI)" with a value between 0 and 255 (a typical value is 100 to 150).

As described above (section on Micro-Lysis Cell-Attack Procedure), the epi-illumination second-energy pathway is opened (by removal of the opaque filter) for a pre-selected time to activate a cell-attack agent within the epi-illumination rectangular microscopic area on the cell micro-sample image. Then, the epi-illumination second-energy pathway is closed. Transilluminated first-energy images of the microsample are then digitized at 30-second intervals over the next 60 minutes (or until there are 5 or fewer intact cells within the rectangular cell-attack area in the image).

After exposure to the epi-illumination second-energy rectangular area of cell-attack activation, the Microscopic area of the cell micro-sample that was exposed becomes brighter and loses its speckled appearance as a function of time in the transilluminated first-energy image, as shown in FIG. 22. This occurs because cells in the microscopic area of the second-energy activated cell-attack lose part or all of their contents and their membranes lose structural integrity as a micro-lysis response to the second-energy activated cell-attack.

The values of the transilluminated first-energy image pixels in the rectangular (approximately 60×50 pixels) microscopic cell-attack area are averaged, and this pixel average is compared in successive digitized images for 60 minutes or until this pixel average rises to a plateau value which does not change by more than ±1% for 3 minutes (6 images). The transillumination first-energy image at 60 minutes, or the first transillumination micro-sample image with a plateau for the average value of the first-energy image pixels in the rectangular microscopic cell-attack area, is defined as the maximal cell-response image. The 30 highest pixel values (10% of total pixels) in the rectangular microscopic cell-attack area of the maximal cell-response image are averaged to define a digital value which represents an image area with no intact cells (called the "total-lysis" first-energy intensity or TLFEI).

The average value for all pixels in the rectangular cell-attack area is defined as a "Response-Area Energy Intensity (t)" for each digitized transilluminated first-energy micro-sample image. These Response-Area Energy Intensities (REI(t)) are converted to relative Response-Area Optical Densities (Response OD(t)) by the following formula:

Response OD(t)=100(TLFEI−REI(t))/(TLFEI−BFEI), where TLFEI is the total-lysis first-energy intensity in the microscopic cell-attack area of the transilluminated micro-sample image, BFEI is the background first-energy intensity for the entire transilluminated micro-sample image, and REI(t) is the response first-energy intensity as a function of time in the microscopic cell-attack area of the transilluminated micro-sample image. The quantity (TLFEI−BFEI) represents the range of the average light intensity for the entire transilluminated first-energy micro-sample image. The zero-time average energy intensity of the rectangular microscopic area before cell-attack (REI(0)) can be larger or smaller than the average background first-energy intensity (BFEI) for the entire transilluminated first-energy micro-sample image. Thus, the zero-time Response-Area OD(0) can be larger or smaller than 100% of the optical density range for the entire transilluminated first-energy micro-sample image. The average Response-Area Energy Intensity in the maximal cell-response image (REI plateau) can be smaller than the total-lysis first-energy intensity (TLFEI) because some intact cells can remain in the rectangular area of the maximal response image. Thus, the minimum plateau Response-Area OD can be larger than zero.

FIGS. 1 and 2 show the first-energy Response-Area optical densities as a function of time from the beginning of a five-minute exposure of human red blood cells to three levels of second-energy cell-attack activation (expressed as Joules per centimeter squared). A second-energy cell-attack activation of 245 J/cm$^2$ gives a Response-Area OD which decreases from a zero-time value of 105% to a minimum plateau value of 18% at 46 minutes after the beginning of the cell-attack activation (FIG. 1). A higher level of cell-attack activation of 401 J/cm$^2$ gives a Response-Area OD which decreases from 102% to 6% at 31 minutes after the beginning of cell-attack activation (FIG. 1), while an even greater cell-attack activation of 638 J/cm$^2$ gives a Response-Area OD which decreases from a zero-time value of 91% to a minimum plateau value of 3% at 37 minutes after the beginning of cell-attack activation (FIG. 2). These data show that changes in second-energy cell-attack activation alter the time-dependent first-energy Response-Area OD curve by affecting the magnitude of the maximal OD change, the slope of the Response-Area OD curve, and the time to the half-maximal change in Response-Area OD.

The variation in zero-time first-energy Response-Area OD occurs before application of the second-energy cell-attack activation and adds statistical variation to the time-dependent first-energy Response-Area OD curve that is produced by the second-energy cell-attack activation. To remove the effect of this attack-unrelated variation in zero-time first-energy Response-Area OD, the following three-step normalization procedure is performed as illustrated in FIG. 3, wherein:

1) The Maximal Micro-Lysis Response (MR) is calculated as the zero-time Response-Area OD (ZROD) minus the Minimum Plateau Response-Area OD (PROD);
   i.e. MR=ZROD−PROD.

2) The Percent Maximal Response (MR%) is calculated as 100 times the Maximal Micro-Lysis Response (MR) divided by the zero-time Response-Area OD (ZROD);
   i.e. MR%=(100)(MR)/(ZROD).

3) The % Response at a specific time t (% Response (t)) is defined as 100 times the quantity, zero-time Response-Area. OD (ZROD) minus the Response-Area OD at time t (ROD(t)), that resultant quantity divided by the Maximal Micro-Lysis Response (MR);
   i.e. % Response (t)=(100)(ZROD−ROD(t))/MR.

The Percent Maximal Response (MR%) is a measure of the percentage number of cells which are eventually ruptured in the rectangular microscopic area that was exposed to the second-energy cell-attack activation. The % Response (t) is a measure of the number of cells which have ruptured as of time t in the rectangular microscopic area that was exposed to the second-energy cell-attack activation, and is expressed as a percentage of the number of cells that are eventually ruptured.

As shown in FIG. 4, the three % Response curves are generated by application of the above formulas to the three Response-Area Optical Density curves in FIGS. 1 and 2. The above-described normalization procedure produces time-dependent % Response curves which change from 0% to 100% after the beginning of the cell-attack activation, irrespective of the variation in the zero-time Response-Area OD (ZROD in FIG. 3). These normalized data show that changes in cell-attack activation alter the time-dependent % Response curves by changing the maximum slope and the time to the half-maximal (50%) value of the curves.

Moreover, FIG. 5 repeats the % Response curve (open circles) of FIG. 4 for the 245 Joules/cm$^2$ cell-attack activation to quantitate precise changes in cell response to specific levels of second-energy cell-attack activation by defining:

1) the response half-time ($T_{1/2}$) as the period from the beginning of second-energy cell-attack activation to the time of the 50-percent response value, and 2) the largest slope of the % Response curve as the Slope at time t=$T_{1/2}$.

$T_{1/2}$ is a measure of average cell sensitivity to membrane rupture by the second-energy cell-attack activation. The largest slope is a measure of the fastest rate of cell membrane rupture at any time after the beginning of the cell-attack activation. This slope provides an index of the "population variation" in individual cell sensitivity to membrane rupture by the cell-attack activation. For example, a population of homogeneous cells, each with exactly the same cell-sensitivity to membrane rupture (i.e. same cell fragility), would give a "step" % Response curve with a zero-value until time equal to $T_{1/2}$, and a 100% value after time equal to $T_{1/2}$. In contrast, a very heterogeneous population of cells, some with very low sensitivity and some with very high sensitivity and some throughout the range from very low to very high sensitivity to membrane rupture, would give a % Response curve with a shallow slope beginning shortly after the beginning of the second-energy cell-attack activation and reaching a 100% value at a time much after the $T_{1/2}$ value.

The Slope of the % Response curve at time equal to $T_{1/2}$ can be obtained in several ways. For example, the value of the first derivative of a polynomial curve-fit to the % Response curve at time equal $T_{1/2}$ would give the slope value of the % Response curve at time equal to $T_{1/2}$. The following gives a simple method for calculation of the Slope of the % Response curve at time equal to $T_{1/2}$:

1) T70 is defined as the period (in minutes) from the beginning of the cell-attack activation to the time when the % Response equals 70%.

2) T30 is defined as the period (in minutes) from the beginning of the cell-attack activation to the time when the % Response equals 30%.

3) Slope at $T_{1/2}$ is defined as 70% minus 30%, that quantity divided by the quantity, T70 minus T30, with units of % Change in Response per Minute (abbreviated as %/MIN);

i.e. Slope at $T_{1/2}$ (%/MIN)=(70–30)/(T70–T30).

This simple method is reasonably accurate because all % Response curves range from 0% to 100% in ordinate value, and all Response curves are approximately linear in the 30% to 70% response range, such as the curve in FIG. 5 for example.

Micro-Lysis of Animal Cells

FIG. 6 shows the first-energy % Response curves (mean±SEM) on day 1 at 7 hours (circles), day 2 (squares), day 3 (triangles), day 4 (diamonds), and day 5 (inverted triangles) after collection of red blood cells from four rabbits. The micro-sample composition was a 4% red blood cell concentration and 2 mg/ml of the cell-attack agent FITC-dextran (150,000 daltons), and the second-energy cell-attack activation was 210 J/cm² for all curves. The first-energy % Response curves are identical to each other when micro-lysis is conducted on cell micro-samples from 7 hours to 5 days after blood collection from rabbits. The % Response curve is shifted to the left of the curves in FIG. 6 when micro-lysis is conducted on cell micro-samples during the first 6 hours after blood collection from rabbits.

FIG. 7 shows first-energy % Response curves (mean±SEM) for the effect of second-energy cell-attack activation of 105 Joules/cm² (open squares), 126 Joules/cm² (filled squares), 159 Joules/cm² (open triangles), 168 J/cm² (filled triangles), 210 J/cm² (open diamonds), and 210 J/cm² (filled diamonds) on rabbit (N=3) red blood cells with micro-sample composition of 4% hematocrit and 2 mg/ml of the cell-attack agent FITC-dextran (150,000 daltons). The second-energy cell-attack activations for the open symbols were achieved by lower epi-illumination power densities for 10 minutes of second-energy exposure, while the cell-attack activations for the filled symbols were achieved by higher epi-illumination power densities for 8 minutes of second-energy exposure. The % Response curve for a lower epi-illumination power density at a longer second-energy exposure time (open symbols) is the same as that for a higher second-energy power density at a shorter second-energy exposure time (filled symbols) when the two respective, power density multiplied by exposure time quantities, give the same energy densities to represent equivalent second-energy cell-attack activations. This observation remains true for any second-energy density, provided that the second-energy exposure time is at least 4 minutes in duration. FIG. 7 also demonstrates that the Slope and $T_{1/2}$ values of the % Response curves are different for different levels of second-energy cell-attack activation. The % Response curves for rabbit red blood cells are also different for different micro-sample concentrations of the cell-attack agent FITC-dextran when the FITC-dextran concentration is below a critical value of 2.0 mg/ml.

FIG. 8 shows the first-energy % Response curves (mean±SEM) for 3% (circles), 4% (triangles), and 5% (squares) concentrations of rabbit (N=4) red blood cells in micro-samples that contained 2 mg/ml of the cell-attack agent FITC-dextran (150,000 daltons) and received a cell-attack activation of 210 J/cm². These % Response curves for rabbit red blood cells are statistically the same for the different micro-sample cell concentrations in the 3 to 5% range, to show that moderate variation in cell concentrations will not change the micro-lysis measurement of cell sensitivity to membrane rupture by second-energy cell-attack activation.

FIG. 9 shows the first-energy % Response curves (mean±SEM) for rabbit (N=3) red blood cells that had been separated from whole blood (circles) and for red blood cells in whole blood that contained plasma and other cells such as platelets and white blood cells (triangles). Micro-sample composition was a 4% red blood cell concentration and 2 mg/ml of the cell-attack agent FITC-dextran (150,000 daltons). These data demonstrate that the first-energy % Response curves for rabbit red blood cells are not affected by the presence of blood plasma or other blood cells (such as white blood cells) in the micro-sample. Thus, the micro-lysis procedure can be applied to whole blood samples, without the need for careful separation of red blood cells.

FIG. 10 shows the first-energy % Response curves (mean±SEM) for micro-lysis of rabbit (N=4) red blood cells on day 5 (circles), on day 5 after the red blood cells had been washed and then reconstituted with buffer and the cell-attack agent FITC-dextran (diamonds), and on day 5 after the red blood cells had been washed and then reconstituted with buffer but not the cell-attack agent FITC-dextran (squares). Micro-sample composition was buffer, 2 mg/ml of FITC-dextran (150,000 daltons), and a 4% red blood cell concentration, and the cell-attack activation was 198 Joules/cm². Cells that were washed on day 5 and reconstituted without the cell-attack agent (FITC-dextran) did not hemolyze when exposed to the second-energy cell-attack activation. Washed cells reconstituted with the original cell-attack agent (FITC-dextran) had the same micro-lysis response as unwashed cells on day five, thus showing that the washed cells could still be affected by the second-energy cell-attack activation but only in the presence of the cell attack agent (FITC-dextran). Thus, FIG. 10 shows that the presence of a cell-attack agent is necessary for the micro-lysis process and that other factors like heat from the second-energy source do not induce hemolysis in this method. FITC-dextran (150,000) is a large molecular weight neutral dextran that does not even traverse endothelial gaps between two cells under non-inflamed conditions. Since washed red blood cells were unresponsive, the data in FIG. 10 demonstrate that the micro-lysis response is not the result of a non-specific second-energy interaction with an intracellular or even intramembrane-bound chemical. The micro-lysis process with FITC-dextran as the cell-attack agent must occur by an interaction of the cell-attack agent and the outside of the cell membrane with subsequent rupture of the cell membrane.

FIG. 11 shows the first-energy % Response curves (mean±SEM) for micro-lysis of rabbit (N=4) red blood cells that had been prepared in standard buffer with glucose and albumin (squares), buffer with glucose but not albumin (filled diamonds), buffer with albumin but not glucose (triangles), and buffer without albumin and glucose (circles). All micro-samples contained 2 mg/ml of the cell-attack agent FITC-dextran (150,000 daltons) and a 4% concentration of red blood cells, and were exposed to a cell-attack activation of 180 J/cm$^2$ (right panel) and 90 J/cm$^2$ (left panel). The % Response Curves for rabbit red blood cells are not altered by removal of albumin from the cell micro-sample. According to scientific literature, removal of albumin changes the shape (deformability) of the red blood cell. Thus, these data show that the micro-lysis process measures cell characteristics other than those that depend solely on cell shape (i.e. deformability). The % Response curves are shifted to the left to reflect greater cell sensitivity to a standardized cell-attack activation when glucose is removed from the cell micro-sample. Cells are very susceptible (an increased Slope and decreased $T_{1/2}$) even to a very low cell-attack activation when glucose is absent as illustrated in the left panel of FIG. 11. According to scientific literature, glucose is necessary for cells to maintain their internal ATP (adenosine triphosphate) levels, and ATP is required for cell metabolism to maintain the structure of the cell membrane. Thus, these data show that the micro-lysis process can detect a reduction in cell membrane ability to maintain the structural integrity of the cell membrane (i.e. a change in cell fragility).

FIG. 12 shows the first-energy % Response curves (mean±SEM) for micro-lysis of rabbit (N=6) cell micro-samples that contained 2 mg/ml of the cell-attack agent FITC-dextran (150,000 daltons), standard buffer, and a 4% concentration of red blood cells which had been previously incubated for one hour with the test chemical diamide at a concentration of 5.0 milliMolar (diamonds), 0.5 mM (squares), 0.05 mM (circles), or 0.00 mM (filled triangles), with cell-attack activations of 180 J/cm$^2$ (right panel) and 90 J/cm$^2$ (left panel). The first-energy % Response curves for rabbit red blood cells are shifted to the left to reflect greater cell sensitivity to a second-energy cell-attack activation when the micro-sample contains cells that have been previously incubated for one hour with the test chemical diamide. These diamide-incubated cells have enhanced susceptibility (increased Slope and decreased $T_{1/2}$) to a very low cell-attack activation as illustrated in the left panel of FIG. 12. According to scientific literature, diamide is a chemical which oxidizes the sulfhydryl groups of proteins in the cell membrane to increase the cross-linking of spectrin which disturbs the protein layers of the cell membrane to increase cell membrane fragility. Thus, these data show that the micro-lysis process can detect an increase in cell fragility which results from a disturbance to the protein layers of the cell membrane.

FIG. 13 shows the first-energy % Response curves (mean±SEM) for micro-lysis of rabbit (N=5) cell micro-samples that contained 2 mg/ml of the cell-attack agent FITC-dextran (150,000 daltons), standard buffer, and a 4% concentration of red blood cells which had been previously incubated for 20 minutes with the test anesthetic Chlorpromazine at a microMolar concentration of 100 μM (circles), 30 μM (diamonds), 10 μM (squares), and 0 μM (filled triangles), with cell-attack activations of 180 J/cm$^2$ (right panel) and 90 J/cm$^2$ (left panel). The first-energy % Response curves for rabbit red blood cells are shifted to the left to reflect greater cell sensitivity to a second-energy cell-attack activation when the micro-sample contains cells that have been previously incubated for 20 minutes with the test anesthetic chlorpromazine. These chlorpromazine-incubated cells are also more susceptible (decreased $T_{1/2}$ but no change in Slope) to very low levels of cell-attack activation as illustrated in the left panel of FIG. 13. According to scientific literature, chlorpromazine, in the concentrations used here, primarily produces stomatocyte formation through an effect of chlorpromazine to alter the arrangement of the lipid bilayer in the cell membrane with less effect on the protein layers in the cell membrane. Thus, these data show that the micro-lysis process can detect an increase in cell membrane fragility which results primarily from a disturbance to the lipid layers of the cell membrane.

FIG. 14 shows the first-energy % Response curves (mean±SEM) for micro-lysis of rabbit (N=6) cell micro-samples that contained 2 mg/ml of the cell-attack agent FITC-dextran (150,000 daltons), standard buffer, and a 4% concentration of red blood cells which had been previously incubated for one hour with a test chemical glutaraldehyde at a concentration of 0.02% (circles with dashed line), 0.01% (diamonds), 0.005% (triangles), 0.0025% (squares with dashed line), 0.00125% (circles), and 0.000% (filled triangles), with a cell-attack activation of 180 J/cm$^2$. The first-energy % Response curves for rabbit red blood cells are shifted to the right with increased $T_{1/2}$ and decreased Slope to reflect less cell sensitivity to cell-attack activation when the micro-sample contains cells that have been previously incubated for one hour with a 0.01% or greater solution of the test chemical glutaraldehyde. According to scientific literature, glutaraldehyde decreases membrane fragility (i.e. a less breakable cell) and increases membrane rigidity (i.e. a less deformable cell). Chlorpromazine increases membrane fragility (i.e. more breakable) without any reported change in membrane rigidity (i.e. unchanged deformability). Diamide increases membrane fragility (i.e. more breakable) and increases membrane rigidity (i.e. less deformable). Thus, comparison of the effect of these three test chemicals as shown in FIGS. 12, 13, and 14 demonstrates that the micro-lysis process measures changes in cell membrane fragility rather than simply cell membrane rigidity, and that the micro-lysis process can distinguish between a change in membrane fragility due to altered lipid layers and a change due to altered protein layers.

A streptozoticin-injected laboratory rat is a widely-used animal model of human insulin-dependent diabetes with elevated blood sugar (hyperglycemia) and glucose spill-over into the urine. Diet manipulation of a laboratory rat is a known animal model of human hypercholesterolemia. FIG. 15 shows the Percent Maximal Response (MR%), the $T_{1/2}$, and the Slope values of the first-energy % Response curves for micro-lysis of red blood cells from 5 normal control Sprague-Dawley laboratory rats (C) at second-energy activations of 248±3.6 J/cm$^2$, 3 streptozoticin-induced insulin-dependent diabetic Sprague-Dawley rats (D) at second-energy activations of 245±4.1 J/cm$^2$ and 6 diet-induced hypercholesterolemic Sprague-Dawley rats (H) at second-energy activations of 249±2.7 J/cm$^2$. All cell micro-samples had a composition of 4 mg/ml of the cell-attack agent FITC-dextran (20,000 daltons), standard buffer, and a 3% concentration of red blood cells. The first-energy % Response curves for red blood cells from normal rats, diabetic rats, and hypercholesterolemic rats have similar Maximal Responses to the micro-lysis process. Red blood cells from the hypercholesterolemic rats have normal $T_{1/2}$ and Slope values. Cells from the diabetic rats have significantly longer $T_{1/2}$ and lower Slope values to indicate a substantial reduction in cell membrane fragility for the diabetic animals. These data demonstrate that the micro-lysis process can detect diseases (such as diabetes) which are thought to alter ion pumps (such as the calcium pumps) in the cell membrane.

Micro-Lysis of Human Cells

FIG. 16 shows the Percent Maximal Response (MR%) and the $T_{1/2}$ and Slope values of the first-energy % Response curves for micro-lysis of 0.5% to 3.0% concentrations of human (N=3) red blood cells in micro-samples that contained 4 mg/ml of the cell-attack agent FITC-dextran (20,000 daltons). One subject received a cell-attack activation of 549±0.3 J/cm$^2$, the second subject received 340±1.1J/cm$^2$ and the third subject received 198±1.3 J/cm$^2$ for all five cell concentrations. Micro-lysis of red blood cells from humans gives the same Percent Maximal Responses for micro-sample cell concentrations in the 1.0% to 3.0% range, the same $T_{1/2}$ values for cell concentrations in the 0.5% to 2.0% range, and the same % Response curve Slopes for cell concentrations in the 0.5% to 3% range as shown in FIG. 16. Micro-lysis of red blood cells from rabbits gives the same first-energy % Response curves for micro-sample cell concentrations in the 3% to 5% range as illustrated in FIG. 8. These data indicate that the micro-lysis process is relatively insensitive to variations in cell concentrations within specific but different concentration ranges for animals and humans.

According to scientific literature, pentoxifylline, a therapeutic drug which increases peripheral blood flow in several human pathologies, increases the "flexibility" of cell membranes to permit easier passage of red blood cells through blood vessels; yet, pentoxifylline does not simply alter cell membrane rigidity (cell deformability). FIG. 17 shows the Percent Maximal Response (MR%) and the $T_{1/2}$ and Slope values of the first-energy % Response curves for micro-lysis of human (N=5) cell micro-samples that contained 4 mg/ml of the cell-attack agent FITC-dextran (20,000 daltons) and a 1% concentration of red blood cells which had been previously incubated at 4° C. FOR ONE HOUR with the therapeutic drug pentoxifylline (PTFX) at concentrations of 10 milliMolar (filled bars), 1 mM (striped bars), and 0 mM (clear bars). One subject received a second-energy cell-attack activation of 658±6.6 J/cm$^2$ three subjects received 329±1.9 J/cm$^2$ and one subject received 196±0.7 J/cm$^2$ for all three pentoxifylline concentrations. FIG. 18 shows the Percent Maximal Response (MR%) and the $T_{1/2}$ and Slope values of the first-energy % Response curves for micro-lysis of human (N=5) cell micro-samples that contained 4 mg/ml of the cell-attack agent FITC-dextran (20,000 daltons) and a 1% concentration of red blood cells which had been previously incubated at 4° C. FOR TWENTY-FOUR HOURS with the therapeutic drug pentoxifylline (PTFX) at concentrations of 10 milliMolar (filled bars), 1 mM (striped bars), and 0 mM (clear bars). One of these subjects received a second-energy cell-attack activation of 641±3.3 J/cm$^2$ three subjects received 330±1.7 J/cm$^2$ and one subject received 205±0.7 J/cm$^2$ for all three pentoxifylline concentrations. Incubation of human red blood cells with pentoxifylline for one hour alters the micro-lysis response of those cells. As the pentoxifylline concentration is increased, there is a progressive (dose-dependent) decrease in the Percent Maximal Response, an increase in $T_{1/2}$, and a decrease in the Slope of the micro-lysis % Response curves as illustrated in FIG. 17. With 24-hour pentoxifylline incubation of red blood cells as shown in FIG. 18, the decrease in the Percent Maximal Response is lost, and the decrease in Slope is partially lost, but the dose-dependent increase in $T_{1/2}$ is still present. These data demonstrate that the micro-lysis process is sensitive to drug-induced alterations in human cell membranes as a function of time after drug treatmentor and that micro-lysis can distinguish between drug-treated and non-treated human cells.

FIG. 19 shows the Percent Maximal Response (MR%) and the $T_{1/2}$ and Slope values of the first-energy % Response curves at second-energy cell-attack activations of A=243±2.9 J/cm$^2$ (clear bars), B=400±3.6 J/cm$^2$ (striped bars), and C=642±4.0 J/cm$^2$ (filled bars) for micro-lysis of red blood cells from four female and three male African-Americans who had no clinical indicators of sickle-cell disease. The cell micro-samples contained 4 mg/ml of the cell-attack agent FITC-dextran (20,000 daltons), a 3% concentration of red blood cells, and buffer. FIG. 20 shows the Percent Maximal Response (MR%) and the $T_{1/2}$ and Slope values of the first-energy % Response curves at second-energy cell-attack activations of A=247±1.1 J/cm$^2$ (clear bars), B=395±5.5 J/cm$^2$ (striped bars), and C=643±4.0 J/cm$^2$ (filled bars) for micro-lysis of red,blood cells from 2 female and 3 male African-Americans with clinical diagnosis of sickle-cell disease but not hemoglobin-F abnormality. The cell micro-samples contained 4 mg/ml of the cell-attack agent FITC-dextran (20,000 daltons), a 3% concentration of red blood cells, and buffer. Normal red blood cells from humans without sickle-cell disease as illustrated in the left panel of FIG. 19 show an eventual 88 to 95% cell rupture (Percent Maximal Response, MR%) after exposure to cell-attack activations across a broad range from 240 J/cm$^2$ to 660 J/cm$^2$. These normal human cells have micro-lysis % Response curves with a progressively decreasing $T_{1/2}$ and a progressively increasing Slope as the second-energy cell-attack activation is increased as shown in FIG. 19. In contrast, red blood cells from humans with sickle-cell disease have a substantially reduced Percent Maximal Response (with a peak at an intermediate cell-attack activation level), a significantly elevated $T_{1/2}$ which is not a function of the cell-attack activation level, and a substantially reduced Slope as is evident in a comparison of FIG. 20 to FIG. 19. These data demonstrate that the micro-lysis process is sensitive to pathologic alterations in human cell membranes, and that micro-lysis provides multiple parameters for detection of human diseases that alter cells.

FIG. 21 shows the Percent Maximal Response (MR%) and the $T_{1/2}$ and Slope values of the first-energy % Response curves at second-energy cell-attack activations of A=253±2.8 J/cm$^2$ (clear bars), B=399±4.6 J/cm$^2$ (striped bars), and C=661±2.1 J/cm$^2$ (filled bars) for micro-lysis of red blood cells from 1 female and 1 male African-American with clinical diagnosis of sickle-cell disease and hemoglobin-F abnormality. The cell micro-samples contained 4 mg/ml of the cell-attack agent FITC-dextran (20,000 daltons), a 3% concentration of red blood cells, and buffer. Red blood cells from humans with a combination of sickle-cell disease and a hemoglobin-F abnormality have a normal Percent Maximal Response, an abnormally high $T_{1/2}$, and a normal Slope at lower cell-attack activations but a reduced Slope at the higher cell-attack activation as is evident in a comparison of FIG. 21 to FIG. 19. These data show that the micro-lysis process is sensitive to combinations of pathologic alterations in human cell membranes. Also these data demonstrate that multiple parameters of the micro-lysis process can differentiate between normal human cells as shown in FIG. 19 and single-disease altered cells as shown in FIG. 20, and can distinguish both of those situations from multiple abnormalities such as those shown in FIG. 21.

The foregoing detailed description is given primarily for clearness of understanding and no unnecessary limitations are to be understood therefrom, for modifications will become obvious to those skilled in the art based upon more recent disclosures and may be made without departing from the spirit of the invention and scope of the appended claims.

I claim:

1. A micro lysis-analysis process for measuring the strength of a cell membrane and detecting abnormalities thereof by applying precise quantities of a first focused photo energy of a selected frequency and energy density to a precise microscopic area of a cell sample containing test cells for measuring as a function of time the precise degree of cell disruption, applying a second focused photo energy of a second selected frequency and energy density to said cell sample thereby photo-activating a photo-activated cell-attack agent for attacking cell membranes in said microscopic area of photo-stimulated cell-attack providing a quantitative, time-related, photo-dose dependent measure of cell fragility, comprising the steps of:

suspending test cells whose membrane strength is to be measured in a solution forming a cell containing solution;

adding an inactive photo-activated cell-attack agent to said cell containing solution, said inactive cell-attack agent comprising molecules absorbing photo energy in a known range of excitation frequencies producing a photosensitive chemical solution;

preparing a micro-sample of said photosensitive chemical solution containing said test cells;

identifying a localized microscopic area within said micro-sample of said photosensitive solution;

applying a specific amount of the first focused photo energy in a cell absorption range to said micro-sample of said photosensitive chemical solution exposing said cells in said micro-sample to said first focused photo energy for a selected period of time for determining photo energy absorption by intact test cells in said localized microscopic area of said micro-sample at any time period;

determining the photo energy absorption and number of intact test cells in said localized microscopic area by measuring the amount of said first focused photo energy passing through said test cells in said micro-sample of said photosensitive chemical solution in said localized microscopic area;

applying a specific amount of the second focused photo energy for a selected time at a second selected wavelength, said second focused photo energy being capable of exciting said inactive cell-attack agent, and said second focused photo energy photo-activating said photosensitive chemical solution forming a cell-reacting medium in said localized microscopic area containing said test cells;

reacting said cell-reacting medium containing said test cells to disrupt cell membranes of said test cells permitting loss of said cell contents and changing the absorption of said first focused photo energy by said test cells in said localized microscopic area:

analyzing the strength of said cell membrane quantitatively by comparing the amount of said first focused photo energy passing through said test cells in said micro-sample after micro-sample exposure to said second focused photo energy, with the amount of said first focused photo energy passing through said test cells in said micro-sample before micro-sample exposure to said second focused photo energy for determining photo energy absorption by remaining intact test cells in said localized microscopic area at selected time intervals; and coordinating and comparing the analyzed cell membrane strength to values for normal cells to measure changes in cell fragility.

2. The micro lysis-analysis process for measuring the strength of a cell membrane as claimed in claim 1, wherein said analyzing step comprises comparing a starting number of cells with the maximum number of test cells disrupted, the time to reach disruption of ½ of the maximum number of test cells to be disrupted, and a maximum rate of cell disruption during said selected time intervals.

3. The micro lysis-analysis process for measuring the strength of a cell membrane as claimed in claim 1, wherein said analyzing step comprises comparing the starting number of test cells with the maximum number of test cells disrupted, the time to reach disruption of ½ of the maximum number of test cells to be disrupted, and a maximum rate of cell disruption.

4. The micro lysis-analysis process for measuring the strength of a cell membrane as claimed in claim 1, including the step of selecting said test cells from the group consisting of red cells, white cells, platelets, and mixture thereof.

5. The micro lysis-analysis process for measuring the strength of a cell membrane as claimed in claim 1, including the step of suspending test cells whose membrane strength are to be measured in a physiologic salt solution of selected osmolality forming a cell containing solution.

6. The micro lysis-analysis process for measuring the strength of a cell membrane as claimed in claim 1, including the step of suspending test cells whose membrane strength is to be measured in a physiologic solution of selected osmolality ranging from about 295 to about 315 milliosmoles forming a cell containing solution.

7. The micro lysis-analysis process for measuring the strength of a cell membrane as claimed in claim 1, including the step of applying said first focused photo energy in time intervals ranging from about 2 minutes to about 60 minutes.

8. The micro lysis-analysis process for measuring the strength of a cell membrane as claimed in claim 1, including the step of applying said second focused photo energy in time intervals ranging from about 2 minutes to about 10 minutes.

9. The micro lysis-analysis process for measuring the strength of a cell membrane as claimed in claim 1, including the step of applying and measuring the amount of said first focused photo energy passing through said micro-sample at 30-second time intervals over a 60-minute period or until there are 5 or fewer intact test cells within said localized microscopic area.

10. The micro lysis-analysis process for measuring the strength of a cell membrane as claimed in claim 1, including the step of preparing a micro-sample of about 25 microliters (µl) of said photosensitive chemical solution.

11. The micro lysis-analysis process for measuring the strength of a cell membrane as claimed in claim 1, including the step of applying a second focused photo energy to photo-activate said inactive cell-attack agent from about 2 minutes to about 10 minutes depending on the particular inactive cell-attack agent selected.

12. The micro lysis-analysis process for measuring the strength of a cell membrane as claimed in claim 1, comprising the step of adding a test substance to said cell containing solution providing test substance induced alterations in cell membranes for determining the effect of said test substance on cell response to micro lysis by applying a standardized photo-activated cell-attack agent and distinguishing between test substance treated and nontreated cells as a function of time after test substance treatment, said test substance being selected from the group consisting of glutaraldehyde, albumin, chlorpromazine, diamide, glucose, albumin, and pentoxyifylline.

13. The micro lysis-analysis process for measuring the strength of a cell membrane as claimed in claim 1, further including the step of adding diamide to said cell containing solution for oxidizing sulfhyryl groups of proteins in the cell membrane to increase membrane fragility and for increasing cross-linking of spectrin to increase membrane rigidity and disrupt cell membrane integrity inducing alterations in cell membranes for determining the effect of said diamide on cell response to micro-photo lysis by applying a standardized photo-activated cell-attack agent and distinguishing between diamide-treated and nontreated cells as a function of time after diamide treatment.

14. The micro lysis-analysis process for measuring the strength of a cell membrane as claimed in claim 1, further including the step of adding chlorpromazine to said cell containing solution producing stomatocytes and altering a lipid bilayer of said cell membrane to disrupt cell membrane integrity by increasing membrane fragility without any change in rigidity of said cell membrane inducing alterations in cell membranes for determining the effect of said chlorpromazine on cell response to micro lysis by applying a standardized photo-activated cell-attack agent and distinguishing between chlorpromazine treated and nontreated cells as a function of time after chlorpromazine treatment.

15. The micro lysis-analysis process for measuring the strength of a cell membrane as claimed in claim 1, further including the step of adding glutaraldehyde to said cell containing solution decreasing membrane fragility and increasing membrane rigidity of said cell membrane inducing alterations in cell membranes for determining the effect of said glutaraldehyde on cell response to micro lysis by applying a standardized photo-activated cell-attack agent and distinguishing between glutaraldehyde treated and nontreated cells as a function of time after glutaraldehyde treatment.

16. The micro lysis-analysis process for measuring the strength of a cell membrane as claimed in claim 1, further including the step of comparing the effect of adding at least one test substance to said cell containing solution for measuring the effect of said test substance on changes in said cell membrane fragility and distinguishing between a change in said membrane fragility due to altered lipid layers and a change in said membrane fragility due to altered protein layers of said cell membrane.

17. The micro lysis-analysis process for measuring the strength of a cell membrane as claimed in claim 1, further comprising the step of selecting human red blood cells as said test cells and comparing said selected red blood cells with control cells for detecting diabetes by changes in the cell-response to micro lysis for changes in membrane integrity caused by diabetes.

18. The micro lysis-analysis process for measuring the strength of a cell membrane as claimed in claim 1, further comprising the step of determining the level of ATP (adenosine triphosphate) in a cell sample by treating the cell sample with known concentrations of said ATP inducing alterations in cell membranes of the test cells for determining the effect of said addition of said ATP on cell response to micro lysis by applying a standardized photo-activated cell-attack agent to the test cells and distinguishing between the integrity of the ATP affected cells and untreated cells before and after the addition of ATP as a function of time after treatment and comparing the membrane integrity of cells in the untreated test cells with the membrane integrity of test cells in the ATP-treated cell containing solution.

19. The micro lysis-analysis process for measuring the strength of a cell membrane as claimed in claim 1, further comprising the step of selecting human red blood cells as said test cells and comparing said selected red blood cells with control human blood cells for detecting sickle-cell anemia by changes in the cell-response to micro lysis for changes in cell membrane integrity caused by said sickle-cell anemia.

20. The micro lysis-analysis process for measuring the strength of a cell membrane as claimed in claim 1, further including the step of selecting a specific photo-activated cell-attack agent for a specific type of test cell.

21. The micro lysis-analysis process for measuring the strength of a cell membrane as claimed in claim 1, including the step of standardizing the osmolality of said test cells and photo-activated cell-attack agent in a standardized buffer solution.

22. The micro lysis-analysis process for measuring the strength of a cell membrane as claimed in claim 1, including the step of varying the concentration of said test cells suspended in said cell containing solution.

23. The micro lysis-analysis process for measuring the strength of a cell membrane as claimed in claim 1, which comprises the steps of testing for a cell membrane altering disease including diabetes, hypercholesterolemia, and sickle-cell anemia.

24. The micro lysis-analysis process for measuring the strength of a cell membrane as claimed in claim 1, further including the step of adding an intracellular membrane-bound specific test drug to said cell containing solution for measuring alterations in cell membrane fragility due to changes in membrane characteristics that are created by a photo-activated cell-attack agent that passes through the cell membrane to attach to internal cell structures where said cell attack agent becomes activated only inside of the test cells.

25. The micro lysis-analysis process for measuring the strength of a cell membrane as claimed in claim 1, further including the step of adding an extracellular membrane-bound specific test drug to said cell containing solution for measuring alterations in cell membrane fragility due to changes in membrane characteristics that are created by a photo-activated cell-attack agent that remains and becomes activated only outside the test cells.

26. The micro lysis-analysis process for measuring the strength of a cell membrane as claimed in claim 1, further including the step of preparing a micro-sample of about 25 microliters (µl) of said photosensitive chemical solution within a covered well means and placing at least one water saturated wick within said well means in close proximity to said micro-sample for preventing dehydration of said micro-sample of said photosensitive chemical solution.

27. The micro lysis-analysis process for measuring the strength of a cell membrane as claimed in claim 1, including the step of producing a cell-response curve having at least four different quantitative measurements of cell membrane integrity for said selected time intervals of cell response to a photo-activated cell-attack agent.

28. The micro lysis-analysis process for measuring the strength of a cell membrane as claimed in claim 1, further comprising the step of determining the level of glucose in the cell containing solution by treating the cell containing solution with known amounts of glucose and comparing the membrane integrity of test cells in the untreated cell containing solution with the membrane integrity of test cells in the treated cell containing solution.

29. A micro lysis-analysis process for measuring the strength of a cell membrane as claimed in claim 1, wherein said photo energy is in a range of about 200 to about 700 nanometers.

30. The micro lysis-analysis process for measuring the strength of a cell membrane as claimed in claim 1, further including the step of selecting said photo-activated cell-attack agent specific to the type of cell to be analyzed.

31. The micro lysis-analysis process for measuring the strength of a cell membrane as claimed in claim 30, further including the step of selecting said photo-activated cell-attack agents from the group consisting of phloxine B, eosin-isothiocyanate, pheophorbide, protoporphyrin, fluorescein isothiocyanate, fluorescein isothiocyanate dextran, and combinations thereof.

32. The micro lysis-analysis process for measuring the strength of a cell membrane as claimed in claim 1, wherein said cell-attack agent is a photo-activated cell-attack fluorochrome.

33. The micro lysis-analysis process for measuring the strength of a cell membrane as claimed in claim 32, further including the step of selecting said photo-activated cell-attack fluorochrome from the group consisting of phloxine B, eosin-isothiocyanate, fluorescein isothiocyanate, fluorescein isothiocyanate dextran, and combinations thereof.

34. The micro lysis-analysis process for measuring the strength of a cell membrane as claimed in claim 1, further comprising the step of selecting human red blood cells as said test cells and comparing said selected red blood cells with control human blood cells for detecting pathologic alterations in human cell membranes by changes in the cell-response to micro lysis for changes in the cell membrane integrity caused by said pathologic alterations.

35. The micro lysis-analysis process for measuring the strength of a cell membrane as claimed in claim 34, further comprising the step of selecting human red blood cells as said test cells and comparing said selected red blood cells with control human blood cells for differentiating between normal human cells and single-disease altered cells and for distinguishing said normal human cells and said single-disease altered cells from multiple-disease altered cells.

36. The micro lysis-analysis process for measuring the strength of a cell membrane as claimed in claim 1, including the step of applying said second focused photo energy to produce a pattern of changes for untreated normal cells with normal membranes and normal metabolism and comparing the strength of the membrane of said untreated normal cells with the strength of the membrane of cells which have been treated by exposure to a known chemical.

37. The micro lysis-analysis process for measuring the strength of a cell membrane as claimed in claim 36, which comprises the steps of adding a chemical which alters a cell membrane including pentoxifylline, diamide, glutaraldehyde, and chlorpromazine.

38. The micro lysis-analysis process for measuring the strength of a cell membrane as claimed in claim 1, further including the step of adding a test drug to said cell containing solution providing drug-induced alterations in cell membranes for determining the effect of said test drug on cells response to micro lysis by applying a standardized photo-activated cell-attack agent and distinguishing between drug-treated and nontreated cells as a function of time after drug treatment.

39. The micro lysis-analysis process for measuring the strength of a cell membrane as claimed in claim 38, wherein said test drug is an intracellular-bound specific test drug.

40. The micro lysis-analysis process for measuring the strength of a cell membrane as claimed in claim 38, further comprising the steps of detecting drug-induced alterations in human cell membranes of a cell sample containing an unknown concentration of a drug by adding known concentrations of said drug to a cell containing solution inducing alterations in said cell membrane for determining the effect of said addition of known concentration of said drug on cell response to micro lysis by applying a standardized photo-activated cell-attack agent before and after the addition of the known concentration of drug.

41. A micro lysis-analysis process for measuring the strength of a cell membrane as claimed in claim 1, including the step of obtaining multiple cell fragility measurements in a single micro-sample by independently reacting said cell attack agent in multiple separated microscopic areas of a single micro-sample and leaving other microscopic areas in the micro-sample as baseline for unactivated cell-attack sample references.

42. A micro lysis-analysis process for measuring the strength of a cell membrane as claimed in claim 41, wherein said cell containing solution further contains other cells of a different type than said test cells.

43. A micro lysis-analysis process for measuring the strength of a cell membrane as claimed in claim 42, wherein said cell containing solution contains different types of cells from blood samples.

44. A micro lysis-analysis process for measuring the strength of a cell membrane as claimed in claim 43, wherein said different type of cells includes red blood cells, white blood cells, and platelets.

\* \* \* \* \*